(12) United States Patent
Yuasa

(10) Patent No.: US 9,044,168 B2
(45) Date of Patent: Jun. 2, 2015

(54) OPHTHALMOLOGIC APPARATUS

(71) Applicant: CANON KABUSHIKI KAISHA, Tokyo (JP)

(72) Inventor: Takashi Yuasa, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/904,643

(22) Filed: May 29, 2013

(65) Prior Publication Data

US 2013/0321765 A1    Dec. 5, 2013

(30) Foreign Application Priority Data

Jun. 1, 2012    (JP) .................................. 2012-126192

(51) Int. Cl.
  *A61B 3/14*    (2006.01)
  *A61B 3/00*    (2006.01)
  *A61B 3/10*    (2006.01)

(52) U.S. Cl.
  CPC ..................................... *A61B 3/1025* (2013.01)

(58) Field of Classification Search
  USPC ................................................. 351/200–246
  See application file for complete search history.

(56) References Cited

U.S. PATENT DOCUMENTS

| | | | |
|---|---|---|---|
| 6,337,993 B1 | 1/2002 | Kishida et al. | |
| 6,655,805 B2 | 12/2003 | Fujieda | |
| 7,527,379 B2 | 5/2009 | Yamaguchi et al. | |
| 7,635,186 B2 | 12/2009 | Kobayashi et al. | |
| 7,736,001 B2 | 6/2010 | Tanaka et al. | |
| 8,469,514 B2 | 6/2013 | Utsunomiya | |
| 8,506,081 B2 | 8/2013 | Matsumoto | |
| 8,596,785 B2 | 12/2013 | Imamura et al. | |
| 8,646,915 B2 | 2/2014 | Nozato | |
| 8,708,489 B2 | 4/2014 | Utagawa | |
| 2001/0056239 A1 | 12/2001 | Ono | |
| 2007/0216866 A1* | 9/2007 | Kobayashi et al. | 351/221 |
| 2009/0303428 A1 | 12/2009 | Tendler | |
| 2012/0019780 A1 | 1/2012 | Nozato | |
| 2012/0033180 A1 | 2/2012 | Pieri et al. | |
| 2013/0321766 A1 | 12/2013 | Morohashi | |
| 2013/0321767 A1 | 12/2013 | Hirose | |
| 2013/0321768 A1 | 12/2013 | Utagawa | |
| 2013/0321769 A1 | 12/2013 | Kusumoto | |

(Continued)

FOREIGN PATENT DOCUMENTS

JP    2002-200043 A    7/2002
JP    2003-126042 A    5/2003

(Continued)

*Primary Examiner* — Mohammed Hasan

(74) *Attorney, Agent, or Firm* — Canon U.S.A., Inc. IP Division

(57) ABSTRACT

An ophthalmologic apparatus includes an aberration measurement unit configured to measure aberration caused by a subject's eye, a correction unit configured to correct aberration of return light from the subject's eye of measurement light applied to the subject's eye caused by the subject's eye based on the aberration measured by the aberration measurement unit, a storage unit configured to store a plurality of combinations of frame rates for obtaining an image of the subject's eye with a number of pixels of the obtained image according to values of the frame rates, and an obtaining unit configured to obtain the image based on the frame rate and the number of pixels in one combination among the plurality of combinations using aberration-corrected return light from the subject's eye.

20 Claims, 9 Drawing Sheets

(56) References Cited

U.S. PATENT DOCUMENTS

2013/0321771 A1* 12/2013 Yuasa ........................... 351/208
2014/0063507 A1    3/2014 Borycki et al.

FOREIGN PATENT DOCUMENTS

| JP | 2004-033275 A | 2/2004 |
| JP | 2010-259543 A | 11/2010 |

* cited by examiner

OPHTHALMOLOGIC APPARATUS

BACKGROUND OF THE INVENTION

1. Field of the Invention

The present invention relates to an ophthalmologic apparatus.

2. Description of the Related Art

A scanning laser ophthalmoscope (SLO), which is an ophthalmologic apparatus utilizing a principle of a confocal laser microscope, can perform raster scanning on, for example, a fundus of a subject's eye with a laser that is measurement light, and obtains a planar image from intensity of its return light from the subject's eye with high resolution at a high speed. Such an apparatus for capturing a planar image is referred to as SLO apparatus in descriptions below.

There is known a technology for measuring aberration caused by a subject's eye by a wavefront sensor in real time, and correcting the aberration caused by the subject's eye by a wavefront correction device. Japanese Patent Application Laid-Open No. 2010-259543 discusses an adaptive optics SLO (hereinafter, may be referred to as AOSLO apparatus) including an adaptive optical system for correcting the aberration by the wavefront correction device. This technique enables the adaptive optics SLO to obtain a planar image of high lateral resolution (See Japanese Patent Application Laid-Open No. 2010-259543). By continuously capturing the planar image via the above-described AOSLO apparatus, a flow of blood cells (blood flow rate) in a fundus blood vessel can be recorded. In addition, the number and shapes of visual cells can be measured from a fundus visual cell image in a certain area.

To accurately record the blood flow rate, an imaging frame rate is faster, the better. In addition, as an imaging range for measuring the visual cells is wider, images more useful for diagnosis can be obtained.

However, when the frame rate or the imaging range is set to an arbitrary value, there is a possibility that signal intensity obtained by a detector will be deteriorated depending on the characteristics of the detector, such as frequency characteristics, used for imaging.

SUMMARY OF THE INVENTION

The present invention is directed to prevention of deterioration of signal intensity obtained by a detector. Not limited to this, the present invention is also directed to operations and effects obtained by exemplary embodiments of the present invention described below and not achieved by the conventional art.

According to an aspect of the present invention, an ophthalmologic apparatus includes an aberration measurement unit configured to measure aberration caused by a subject's eye, a correction unit configured to correct aberration of return light from the subject's eye of measurement light applied to the subject's eye caused by the subject's eye based on the aberration measured by the aberration measurement unit, a storage unit configured to store a plurality of combinations of frame rates for obtaining an image of the subject's eye with a number of pixels of the obtained image according to values of the frame rates, and an obtaining unit configured to obtain the image based on the frame rate and the number of pixels in one combination among the plurality of combinations using aberration-corrected return light from the subject's eye.

According to the present invention, the deterioration of signal intensity obtained by a detector can be prevented.

Further features of the present invention will become apparent from the following description of exemplary embodiments with reference to the attached drawings.

DESCRIPTION OF THE EMBODIMENTS

Various exemplary embodiments, features, and aspects of the invention will be described in detail below with reference to the drawings. The present invention is not limited to the exemplary embodiments described below. Various changes and modifications can be made within the scope of the present invention.

According to the present exemplary embodiment, an AOSLO apparatus according to the present invention will be described as an ophthalmologic apparatus. The AOSLO apparatus includes an adaptive optical system and captures a high lateral resolution planar image (hereinafter, may be referred to as an AOSLO image) of a fundus of a subject's eye.

For the purpose of assisting obtaining of an AOSLO image, the AOSLO apparatus includes a wide field scanning laser ophthalmoscopy (WFSLO) unit for capturing a wide field angle planar image (hereinafter, may be referred to as a WFSLO image). The AOSLO apparatus further includes an anterior eye portion observation unit for understanding an incident position of measurement light, and a fixation lamp unit for guiding a line of sight to adjust an imaging point.

In the AOSLO apparatus according to the present exemplary embodiment, optical aberration caused by a subject's eye is corrected using a spatial light modulator to obtain a planar mage. Thus, a good planar image reduced in influence of a diopter of the subject's eye or the optical aberration caused by the subject's eye can be obtained.

According to the present exemplary embodiment, the AOSLO device includes the adaptive optical system to capture the high lateral resolution planar image. However, the adaptive optical system may not be necessary as long as the configuration of the optical system can realize high resolution.

<Overall Configuration of Apparatus>

Figure 1A:
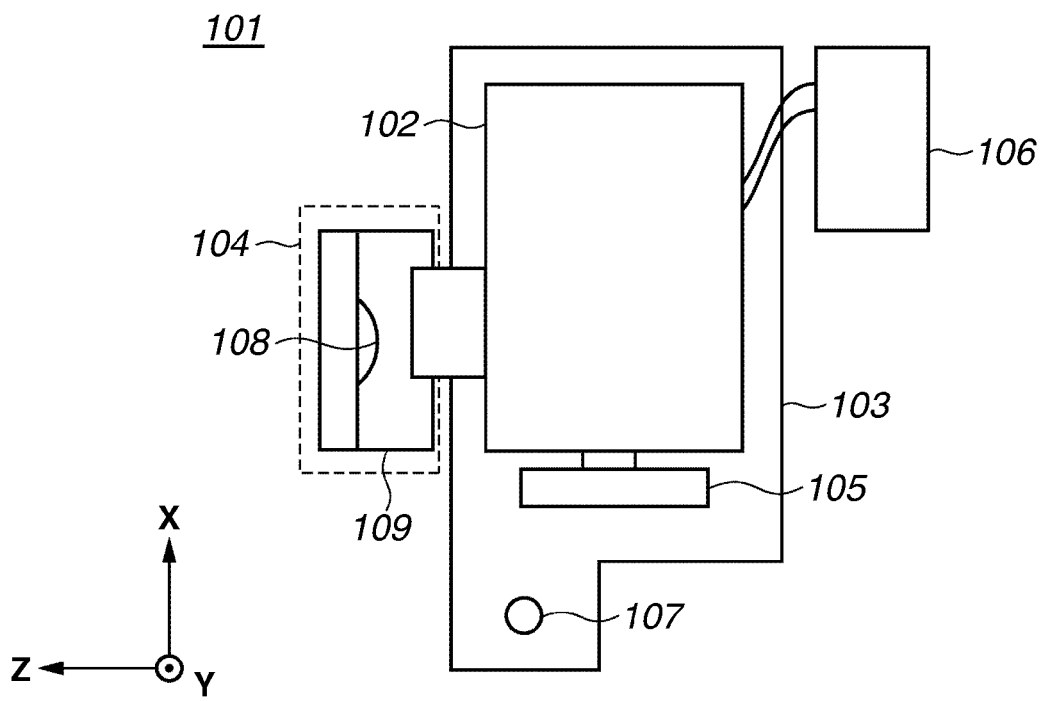
FIGS. 1A and 1B illustrate an example of an entire configuration of an AOSLO apparatus according to an exemplary embodiment of the present invention.
Figure 1B:
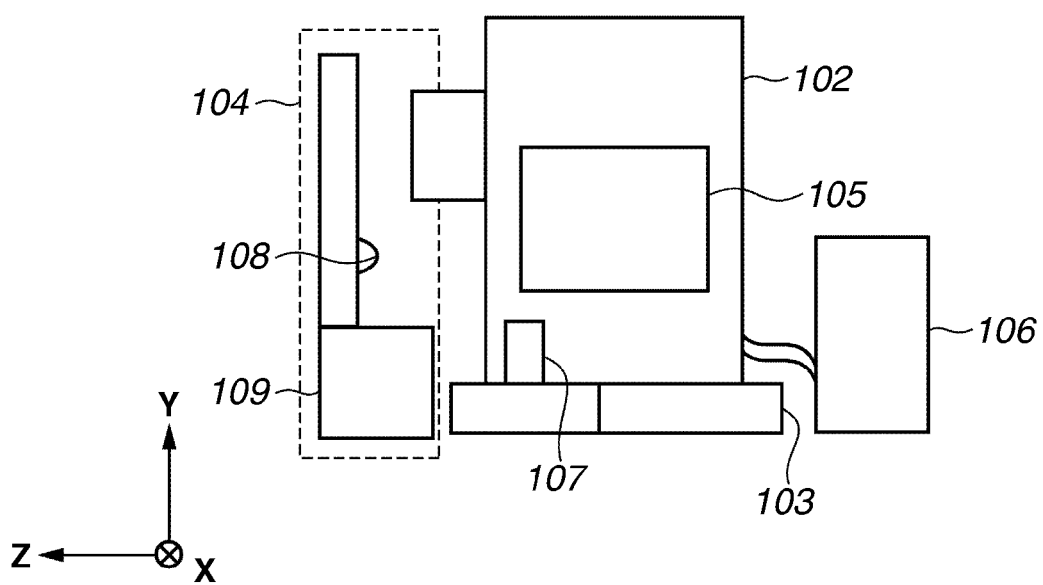

Referring to FIGS. 1A and 1B, a schematic configuration of an AOSLO apparatus 101 according to the present exemplary embodiment will be described. FIGS. 1A and 1B illustrate an example of an entire configuration of the AOSLO apparatus 101 according to the present exemplary embodiment. FIG. 1A is a top view of the AOSLO apparatus 101, and FIG. 1B is a side view of the AOSLO apparatus 101 according to the present exemplary embodiment. According to the present exemplary embodiment, the AOSLO apparatus 101 seen from a face rest member 104 side is a front.

The AOSLO apparatus 101 includes a head unit 102, a stage unit 103, the face rest member 104, a liquid crystal monitor 105, a control PC 106, and a joy stick 107.

The head unit 102 includes a unit for capturing an image of, for example, a subject's eye, and a main optical system. The included optical system will be described in detail below. According to the present exemplary embodiment, the head unit 102 is installed on the stage unit 103.

The stage unit 103 moves the head unit 102 in horizontal and vertical directions according to an operation of the joy stick 107 made by an examiner. For example, the head unit 102 can be moved in the horizontal direction (X and Z directions) by pulling forward the joy stick 107, and in the vertical direction (Y direction) by rotating the joy stick 107.

A face of a subject can be mounted on the face rest member 104, and a position of the subject's eye can be adjusted by moving the face rest member 104. More specifically, the face rest member 104 includes a chin rest 108 on which the subject rests his/her chin, and a chin rest driving unit 109 for moving the chin rest 108 by an electric stage.

The liquid crystal monitor 105 can display various pieces of information and display, for example, an operation screen of the AOSLO apparatus 101. The liquid crystal monitor 105 corresponds to an example of a display unit. According to the present exemplary embodiment, the liquid crystal is used for a monitor. However, the monitor is not limited to the liquid crystal, and any type can be used as long as it can display information. The liquid crystal monitor 105 may have a touch panel function.

The control PC 106 controls the entire AOSLO apparatus 101.

The joy stick 107 receives an instruction from an examiner. For example, the head unit 102 can be moved in the horizontal direction by pulling forward the joystick 107, and in the vertical direction by rotating the joy stick 107. When the liquid crystal monitor 105 has a touch panel function, and the head unit 102 can be moved by an operation on the touch panel, there is no need to install any joy stick 107.

The liquid crystal monitor 105 is located on the side surface of the head unit 102. However, the position of the liquid crystal monitor 105 is not limited to this, and the liquid crystal monitor 105 can be located at another position such as the rear surface of the head unit 102. Further, the position of the liquid crystal monitor 105 can be fixed or movable. The control PC 106 is located outside the head unit 102. However, not limited to this position, the control PC 106 may be located in the head unit 102 or the stage unit 103. The joy stick 107 is located on the side surface of the head unit 102. However, not limited to this position, the joy stick 107 can be located at another position such as the rear surface of the head unit 102.

<Configuration of Optical System>

Figure 2:
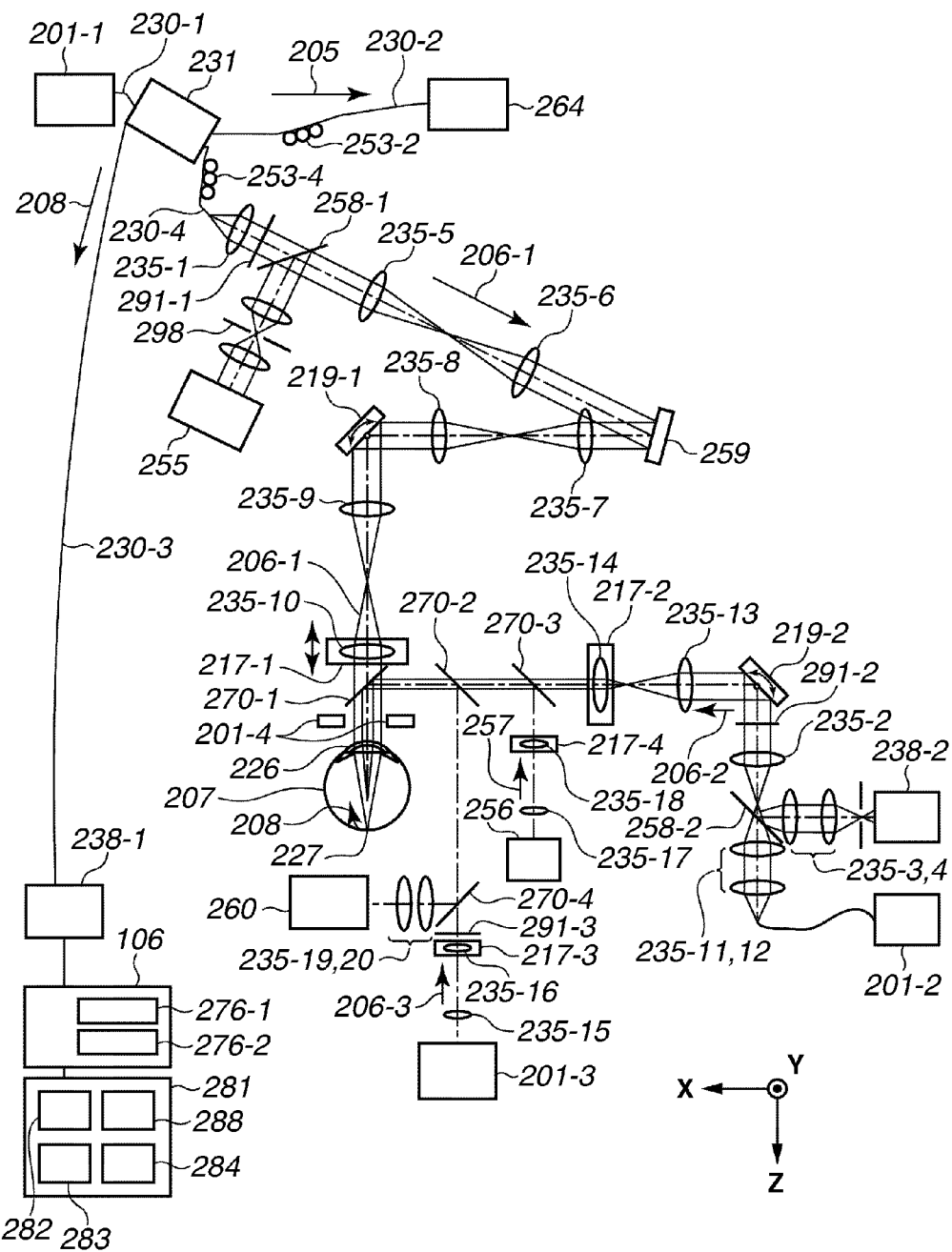
FIG. 2 illustrates an example of a configuration of an optical system of the AOSLO apparatus according to the exemplary embodiment of the present invention.

Next, referring to FIG. 2, the optical system built into the head unit 102 will be specifically described. All the optical systems illustrated in FIG. 2 do not need to be built into the head unit 102. For example, the optical systems illustrated in FIG. 2 can be built into the head unit 102 and the stage unit 103. FIG. 2 illustrates an example of a configuration of the optical system of the AOSLO apparatus 101 according to the present exemplary embodiment.

According to the present exemplary embodiment, the entire optical system is configured by a refractive optical system mainly using lenses. However, a reflective optical system using a spherical mirror in place of the lens can be used.

The optical system illustrated in FIG. 2 includes an AOSLO unit, a beacon unit, a WFSLO unit, a fixation lamp unit, and an anterior eye portion observation unit.

The AOSLO unit includes a light source 201-1, single mode fibers 230-1, 230-3, and 230-4, an optical fiber 230-2, an optical coupler 231, polarization controllers 253-2 and 253-24, and a shutter 291-1. The AOSLO unit further includes lenses 235-1, 235-5, 235-6, 235-7, 235-8, 235-9, and 235-10, a beam splitter 258-1, a spatial light modulator 259, and an X-Y scanner 219-1. The AOSLO unit further includes a dichroic mirror 270-1, an electric stage 217-1, a light amount measurement apparatus 264, and a detector 238-1.

The beacon unit includes a light source 201-3, lenses 235-5, 235-6, 235-7, 235-8, 235-9, 235-10, 235-15, and 235-16, an X-Y scanner 219-1, a spatial light modulator 259, and a pinhole 298. The beacon unit further includes a shutter 291-3, dichroic mirrors 270-1, 270-2, and 270-4, electric stages 217-1 and 271-3, a beam splitter 258-1, and a wavefront sensor 255.

The WFSLO unit includes a light source 201-2, lenses 235-2, 235-3, 235-4, 235-11, 235-12, 235-13, and 235-14, a beam splitter 258-2, and an X-Y scanner 219-1. The WFSLO unit further includes an electric stage 217-2, dichroic mirrors 270-1, 270-2, and 270-3, a shutter 291-2, and a detector 238-2.

The fixation lamp unit includes a fixation lamp 256, lenses 235-17 and 235-18, dichroic mirrors 270-1, 270-2, and 270-3, and an electric stage 217-4.

The anterior eye portion observation unit includes an anterior eye portion illumination light source 201-4, dichroic mirrors 270-1, 270-2, and 270-4, lenses 235-19 and 235-20, and a charge-coupled device (CCD) camera 260.

<AOSLO Unit>

The AOSLO unit obtains an AOSLO image.

First, the light source 201-1 will be described. The light source 201-1 is a super luminescent diode (SLD) that is a representative low-coherent light source. As an example, a center wavelength of a light emitted from the light source 201-1 is 840 nm, and a band width (full width at half maximum) is 50 nm. A value of the center wavelength is determined in view of, for example, losses caused by light absorption of the subject's eye (crystal lens or corpus vitreum). Generally, losses caused by light absorption are smaller near 840 nm than a proximate wavelength. In this case, the low-coherent light source is selected to obtain a planar image having limited speckle noise. The SLD is selected as the light source in the present exemplary embodiment. However, any type of a light source can be used as long as it can emit low-coherent light, and an amplified spontaneous emission (ASE) or the like can be used.

For the wavelength, near-infrared light is suitable in view of eye measurement. Further, a shorter wavelength is desirable because the wavelength affects horizontal resolution of the obtained planar image and, in this case, for example, the wavelength is 840 nm. Other wavelengths can be selected depending on measured portions of the observation target.

The light emitted from the light source 201-1 is divided into reference light 205 and measurement light 206-1 at a rate of 90:10 via the single mode fiber 230-1 and the optical coupler 231. More specifically, the light emitted from the light source 201-1 is divided into the reference light 205 and the measurement light 206-1 by the optical coupler 231. The branch ratio by the optical coupler 231 is not limited to this value.

<Reference Light 205>

Next, an optical path of the reference light 205 will be described.

The reference light 205 divided by the optical coupler 231 enters into the light amount measurement apparatus 264 via the optical fiber 230-2 including a polarization controller 253-2 for controlling light polarization. The light amount measurement apparatus 264 is used for measuring an amount of the reference light 205 and monitoring an amount of the measurement light 206-1. For example, when a measured value of the light amount measurement apparatus 264 exceeds a predetermined threshold value, the control PC 106 determines that a safe light amount is exceeded, and limits entry of the light emitted from the light source 201-1 into the subject's eye.

<Measurement Light 206-1>

Next, an optical path of the measurement light 206-1 will be described.

The measurement light 206-1 divided by the optical coupler 231 is guided to the lens 235-1 via the single mode fiber 230-4 including a polarization controller 253-4 for controlling light polarization. The measurement light 206-1 is adjusted to be a parallel beam having, for example, a beam diameter of 4 mm by the lens 235-1. The value of the beam diameter is only an example, and thus in no way limitative. Then, the measurement light 206-1 reaches the beam splitter 258-1 via the shutter 291-1. The shutter 291-1 can control whether to enter the light emitted from the light source 201-1 to the subject's eye 207.

The measurement light 206-1 passes through the beam splitter 258-1 and the lenses 235-5 and 235-6 to enter into the spatial light modulator 259. The beam splitter 258-1 transmits the light output from the light source 201-1 to the subject's eye 207 and a return light from the subject's eye 207 by the light source 201-1 while reflecting a light emitted from the light source 201-3 and returned from the subject's eye 207 to the wavefront sensor 255. In other words, the beam splitter 258-1 has characteristics of transmitting light of wavelengths 800 to 880 nm while reflecting light of other wavelengths.

According to the present exemplary embodiment, the reflective spatial light modulator is used as the aberration correction device. However, a transmissive spatial light modulator or a variable shape mirror can be used.

The spatial light modulator 259 is controlled by the control PC 106 via a spatial light modulator driver 288 in the driver unit 281. In other words, the spatial light modulator driver 288 is electrically connected to the spatial light modulator 259. The driver unit 281 illustrated in FIG. 2 is located outside the control PC 106. However, the driver unit 281 can be disposed within the control PC 106.

Then, the measurement light 206-1 is modulated by the spatial light modulator 259, and passed through the lenses 235-7 and 235-8 to enter into the mirror of the XY scanner 219-1. For simplicity, the XY scanner 219-1 is illustrated as one mirror. In reality, however, two mirrors are arranged close to each other as an X scanner and a Y scanner, and raster scanning is performed on a retina 227 in a direction vertically to the optical axis. A center of the measurement light 206-1 is adjusted so as to coincide with a mirror rotational center of the XY scanner 219-1.

The X scanner is a scanner to scan the measurement light 206-1 in a direction parallel to a paper surface, and a resonance scanner is used. For example, a driving frequency of the X scanner is about 7.9 kHz. The Y scanner is a scanner to scan the measurement light 206-1 in a direction vertical to the paper surface, and a Galvano scanner is used. For example, a driving waveform is a saw-tooth wave, a frequency is about 32 Hz, and a duty ratio is 16%. The driving frequency of the Y scanner is an important parameter for determining a frame rate for capturing an AOSLO image. The frame rate for capturing the AOSLO image can be changed by changing the driving frequency of the Y scanner.

The XY scanner 219-1 is controlled from the control PC 106 via an optical scanner driver 282 in the driver unit 281. In other words, the optical scanner driver 282 is electrically connected to the XY scanner 219-1.

The measurement light 206-1 scanned by the XY scanner 219-1 is guided to the subject's eye 207 that is an observation target via the lenses 235-9 and 235-10 and the dichroic mirror 270-1. In other words, the XY scanner 219-1 corresponds to an example of a scanning unit for scanning a subject's eye with measurement light.

The lenses 235-9 and 235-10, which are optical systems for scanning the retina 227, has a function of scanning the retina 227 with the measurement light 206-1 with a pupil center of the subject's eye 207 set as a supporting point.

A beam diameter of the measurement light 206-1 is 4 mm. However, the beam diameter can be larger to obtain an optical image of higher resolution, and a beam diameter can be less than 4 mm when high resolution is not necessary. In other words, the beam diameter is not limited to 4 mm.

The electric stage 217-1 can be moved in directions indicated by an arrow in FIG. 2 to move a position of the accompanying lens 235-10, thereby adjusting a focus.

The electric stage 217-1 is controlled from the control PC 106 via an electric stage driver 283 in the driver unit 281. In other words, the electric stage driver 283 is electrically connected to the electric stage 217-1. By adjusting the position of the lens 235-10, the measurement light 206-1 is focused on a predetermined layer of the retina 227 of the subject's eye 207, thus observation can be performed. The apparatus can even deal with refraction abnormality in the subject's eye 207.

The measurement light 206-1 passed through the lens 235-10 enters into the subject's eye via the dichroic mirror 270-1.

The dichroic mirror 270-1 transmits the light output from the light source 201-1 to the subject's eye and a light emitted from the light source 201-1 and returned from the subject's eye. On the other hand, the dichroic mirror 270-1 reflects the light output from the light source 201-2 to the subject's eye, the light emitted from the light source 201-2 and returned from the subject's eye, and the light emitted from the anterior eye portion illumination light source 201-4 and returned from the subject's eye. Further, The dichroic mirror 270-1 reflects the light from the fixation lamp 256. Furthermore, the dichroic mirror 270-1, for example, reflects a half and transmits a half of the light output from the light source 201-3 to the subject's eye and the light emitted from the light source 201-3 and returned from the subject's eye. A ratio of reflection and transmission is not limited to 1:1. In other words, the dichroic mirror 270-1 has characteristics of transmitting light of wavelengths 800 to 880 nm while reflecting a half and transmitting a half of light of wavelengths 750 to 770 nm. The dichroic mirror 270-1 enables separation of the light emitted from the light source 201-1 and the light source 201-3 from the light emitted from the other light sources.

The measurement light 206-1, which has entered into the subject's eye 207, is converted into return light 208 by reflection or scattering from the retina 227 to reversely travel on the optical path, and is guided again to the optical coupler 231.

Then, the return light reaches the detector 238-1 via the single mode fiber 230-3. In other word, the spatial light modulator 259 corresponds to an example of a correction unit for correcting aberration of the return light of the measurement light applied to the subject's eye and returned from the subject's eye, which is occurred at the subject's eye, based on the aberration measured by the aberration measurement unit. For the detector 238-1, for example, an avalanche photodiode (APD) or a photomultiplier tube (PMT) which is a high-speed and high-sensitive optical sensor can be used. However, the detector is not limited to these. The detector 238-1 converts light intensity of the return light 208 into a voltage, and the control PC 106 forms a planar image of the subject's eye 207 using this voltage signal. In other words, the detector 238-1 corresponds to an example of a light receiving unit for receiving the return light from the subject's eye.

<WFSLO Unit>

Next, the WFSLO unit will be described. The WFSLO unit obtains a WFSLO image. The WFSLO unit has a configuration basically similar to that of the AOSLO unit, and thus description of overlapped portions will be omitted.

The WFSLO unit includes the light source 201-2. The light source 201-2 is a SLD as in the case of the AOSLO unit. A center wavelength of the light emitted from the light source 201-2 is 920 nm, and a band width is 20 nm. The SLD is selected as the light source in the present exemplary embodiment. However, any type of a light source can be used as long as it can emit low-coherent light, and an amplified spontaneous emission (ASE) or the like can be used. The wavelength and the bandwidth of the light emitted from the light source 201-2 are not limited to these values. Other values can be employed.

An optical path of measurement light 206-2 emitted from the light source 201-2 will be described. The measurement light 206-2 emitted from the light source 201-2 is guided to the subject's eye 207 that is an observation target via the shutter 291-2, the lens 235-2, the lenses 235-11 to 235-14, the beam splitter 258-2, the XY scanner 219-2, and the dichroic mirrors 270-1 to 270-3. The shutter 291-2 can control whether to enter the light emitted from the light source 201-3 into the subject's eye 207.

The beam splitter 258-2 transmits the light output from the light source 201-2 to the subject's eye while reflecting the light emitted from the light source 201-2 and returned from the subject's eye to the detector 238-2.

The dichroic mirror 270-2 transmits the light output from the light source 201-2 to the subject's eye, the light emitted from the light source 201-2 and returned from the subject's eye, and the light from the fixation lamp 256. On the other hand, the dichroic mirror 270-2 reflects the light output from the light source 201-3 to the subject's eye and the light emitted from the light source 201-3 and returned from the subject's eye. The dichroic mirror 270-2 reflects the light output from the anterior eye portion illumination light source 201-4 and returned from the subject's eye 207. In other words, the dichroic mirror 270-2 has characteristics of reflecting light of wavelengths 700 to 880 nm while transmitting light of other wavelengths. The dichroic mirror 270-2 enables separation of the light emitted from the light source 201-3 and the anterior eye portion illumination light source 201-4 from the light emitted from the light source 201-1 and the fixation lamp 256.

The dichroic mirror 270-3 transmits the light output from the light source 201-2 to the subject's eye, the light emitted from the light source 201-2 and returned from the subject's eye, and the light from the fixation lamp 256. On the other hand, the dichroic mirror 270-3 reflects the light output from the fixation lamp 256 to the subject's eye. In other words, the dichroic mirror 270-3 has characteristics of transmitting lights of wavelengths of 700 nm or more while reflecting light of other wavelengths. The dichroic mirror 270-3 enables separation of the light emitted from the fixation lamp 256 from the light emitted from the light source 201-2.

In FIG. 2, for simplicity, the XY scanner 219-2 is illustrated as one mirror. In reality, however, two mirrors are arranged close to each other as an X scanner and a Y scanner, and raster scanning is performed on the retina 227 in a direction vertically to the optical axis.

The X scanner as a component of the XY scanner 219-2 is a scanner to scan the measurement light 206-2 in a direction parallel to a paper surface, and a resonance scanner is used. For example, a driving frequency is about 3.9 kHz. The Y scanner is a scanner to scan the measurement light 206-2 in a direction vertical to the paper surface, and a Galvano scanner is used. For example, a driving waveform is a saw-tooth wave, a frequency is about 15 Hz, and a duty ratio is 16%. The driving frequency of the Y scanner is an important parameter for determining a frame rate of a WFSLO image. The XY scanner 219-2 is controlled from the control PC 106 via the optical scanner driver 282 in the driver unit 281. In other words, the optical scanner driver 282 is electrically connected to the XY scanner 219-2.

The optical system is configured so that a beam diameter of the measurement light 206-2 is 1 mm. However, the beam diameter can be larger to obtain an optical image of higher resolution, and the beam diameter can be less than 1 mm when high resolution is not necessary. In other words, the beam diameter is not limited to 1 mm.

The measurement light 206-2, which has entered into the subject's eye 207, is converted into the return light 208 by reflection or scattering from the retina 227, and reaches the detector 238-2 via the dichroic mirrors 270-1 to 270-3, the lenses 235-13 and 235-14, the lenses 235-2 to 235-4, the XY scanner 219-2, and the beam splitter 258-2.

<Beacon Unit>

Next, the beacon unit for measuring aberration generated in the subject's eye 207 will be described.

The beacon unit includes the light source 201-3. A center wavelength of the light emitted from the light source 201-3 is 760 nm, and a band width is 20 nm. The wavelength and the bandwidth of the light emitted from the light source 201-3 are not limited to these values, and other values can be employed.

Measurement light 206-3 emitted from the light source 201-3 is guided to the subject's eye 207 that is the observation target via the shutter 291-3, the lenses 235-15 and 235-16, and the dichroic mirrors 270-1, 270-2, and 270-4. To prevent reflection from a cornea 226, the measurement light 206-3 is decentered from, for example, the center of the subject's eye 207 to enter. The shutter 291-3 can control whether to enter the light emitted from the light source 201-3 into the subject's eye 207.

The dichroic mirror 270-4 transmits the light output from the light source 201-3 to the subject's eye 207 while reflecting the light emitted from the anterior eye portion illumination light source 201-4 and returned from the subject's eye to the CCD camera 260. In other words, the dichroic mirror 270-4 has characteristics of transmitting light of wavelengths of 750 nm or more while reflecting light of other wavelengths. The dichroic mirror 270-4 enables separation of the light emitted from the anterior eye portion illumination light source 201-4 from the light emitted from the light source 201-3.

A part of the return light 208 by the light source 201-3 enters into the wavefront sensor 255 via the beam splitter 258-1 and the pinhole 298, and aberration of the return light 208 generated in the subject's eye is measured. In other words, the wavefront sensor 255 corresponds to an example of an aberration measurement unit for measuring aberration caused by the subject's eye using the return light of first measurement light from the subject's eye. The pinhole 298 is provided for the purpose of blocking off unnecessary lights other than the return light 208. The wavefront sensor 255 is electrically connected to the control PC 106.

The wavefront sensor 255 is a Shack-Hartmannn wavefront sensor, and a measurement range is −10 D to +5 D. The obtained aberration is expressed by using Zernike polynomial which indicates aberration at the subject's eye 207. The Zernike polynomial includes a tilt term, a defocus term, an astigmatism term, a coma term, and a trifoil term.

The lenses 235-5 to 235-10 are arranged so that the cornea 226, the XY scanner 219-1, the wavefront sensor 255, and the spatial light modulator 259 can be optically conjugate with one another. Thus, the wavefront sensor 255 can measure the aberration caused by the subject's eye 207. The spatial light modulator 259 can correct the aberration caused by the subject's eye 207.

<Fixation Lamp>

A light flux 257 from the fixation lamp 256 has a function of prompting fixation or rotation of the subject's eye 207.

Figure 3:
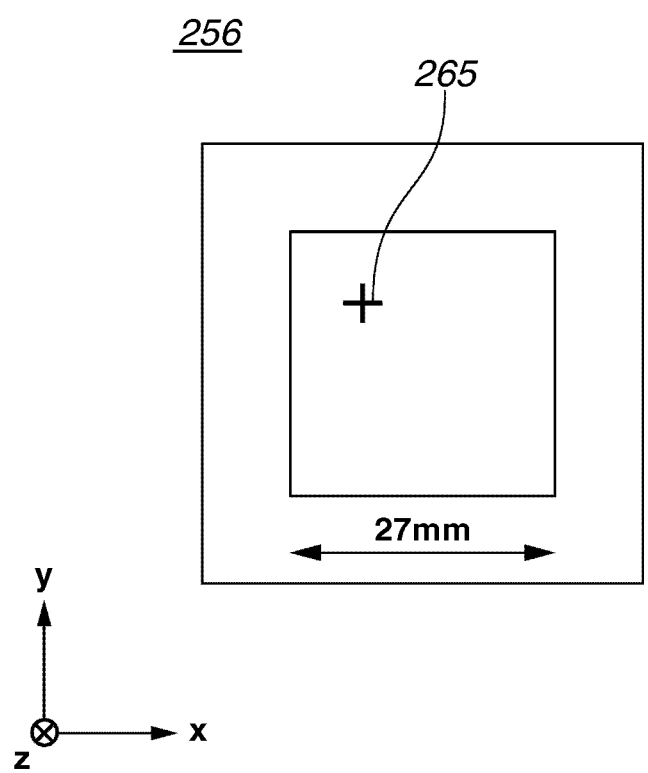
FIG. 3 illustrates an example of a fixation lamp according to the exemplary embodiment of the present invention.
Figure 4:
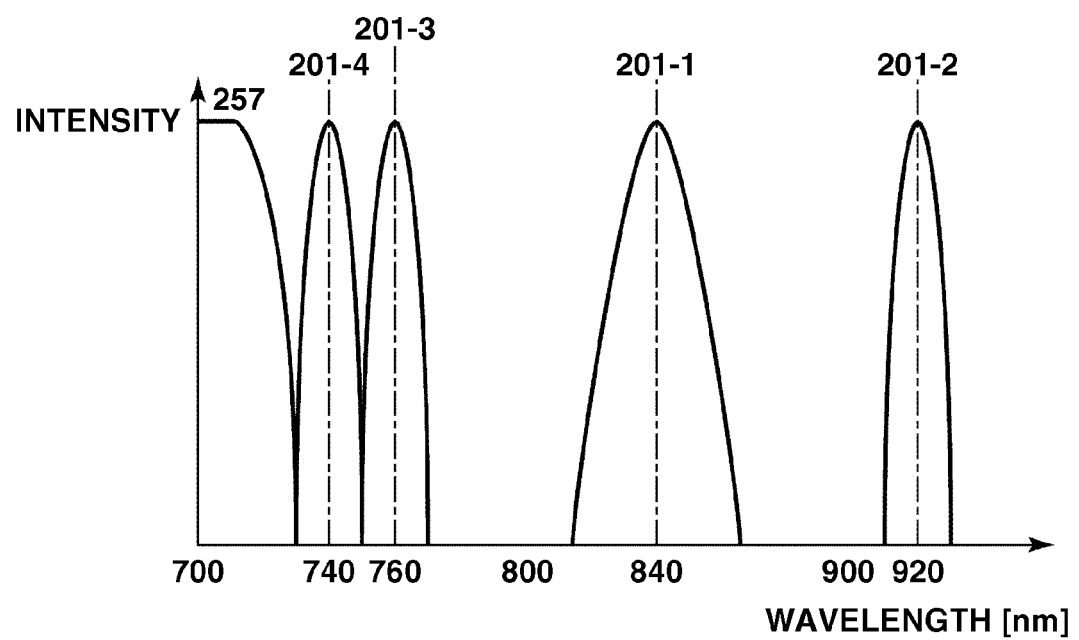
FIG. 4 illustrates an example of a wavelength distribution of measurement light of the AOSLO apparatus according to the exemplary embodiment of the present invention.

The fixation lamp 256 includes a light emitting display module, and has a display surface (27 mm, 128*128 pixels) on an XY plane. A liquid crystal, an organic electroluminescence (EL) or a light emitting diode (LED) array can be used. The subject's eye 207 gazes the light flux 257 from the fixation lamp 256, and accordingly fixation or rotation of the subject's eye 207 is prompted. On the display surface of the fixation lamp 256, a cross pattern is displayed while blinking at an arbitrary lighting position 265 for example, as illustrated in FIG. 3. The light flux 257 emitted from the fixation lamp 256 is a visible light. As illustrated in FIG. 4, a waveform of a part of the light flux 256 (e.g., a red wavelength included in the visible light) is equal to or more than 700 nm.

The light flux 257 from the fixation lamp 256 is guided to the retina 227 via the lenses 235-17 and 235-18 and the dichroic mirrors 270-1 to 270-3. The lenses 235-17 and 235-18 are arranged so that the display surface of the fixation lamp 256 and the retina 227 can be optically conjugate with each other. The fixation lamp 256 is controlled from the control PC 106 via a fixation lamp driver 284 in the driver unit 281. In other words, the fixation lamp driver 284 is electrically connected to the fixation lamp 256.

A size of the display surface of the fixation lamp 256 and the number of pixels are not limited to the above-described values, and other values can be employed. In the above-described example, the cross fixation pattern is employed. However, not limited to this shape, other shapes can be employed.

<Anterior Eye Portion Observation Unit>

Next, the anterior eye portion observation unit will be described. The anterior eye portion observation unit obtains an anterior eye portion image of the subject's eye.

The anterior eye portion illumination light source 201-4 is a LED having, for example, a center wavelength of 740 nm. For example, a band width is several ten nm. The center wavelength and the band width are not limited to these values. The light emitted from the anterior eye portion illumination light source 201-4 illuminates the subject's eye 207, and its reflected light enters into the CCD camera 260 via the dichroic mirrors 207-1, 207-2, and 207-4 and the lenses 235-19 and 235-20.

<Focus and Astigmatism Correction>

As described above, the optical system built into the head unit 102 includes the AOSLO unit, the WFSLO unit, the beacon unit, the fixation lamp unit, and the anterior eye portion observation unit. The AOSLO unit, the WFSLO unit, the beacon unit, and the fixation lamp unit individually include the respective electric stages 217-1 to 217-4, and the four electric stages are interlockingly moved. However, when focus positions are individually adjusted, the positions can be adjusted by individually moving the electric stages.

The lens 235-10 can be replaceable, and a spherical lens or a cylindrical lens can be used according to the aberration (refractive abnormality) caused by the subject's eye 207. In addition, the lens 235-10 is not limited to one lens, and a plurality of lenses can be installed in combination.

<Shutter>

The AOSLO unit, the WFSLO unit, and the beacon unit respectively include the shutters 291-1 to 291-3 on the optical paths of the light sources 201-1 to 201-3, and the shutters 291-1 to 291-3 can control whether to enter the light into the subject's eye 207 by individually blocking off the light. Opening and closing of the shutters 291-1 to 291-3 are controlled by the control PC 106 (i.e., a driving/control unit 114).

According to the present exemplary embodiment, the shutter is used for controlling the light entering into the subject's eye 207. However, not limited to the shutter, the light entering into the subject's eye 207 can be controlled by changing the optical path by a mirror or the like. The light entering into the subject's eye 207 can be controlled by directly turning ON/OFF the light sources 201. In addition, an attenuation filter may be disposed in place of the shutter, and incidence and limitation of incidence on the subject's eye 207 can be switched by insertion and removal of the attenuation filter in/from the optical path. Similarly, the anterior eye portion observation unit and the fixation lamp unit can be controlled by turning ON/OFF the light source 201-4 and a light-emitting display module. When the shutters 291-1 to 291-3 are used, the incidence of the light into the subject's eye 207 can be controlled while the light sources 201-1 to 201-3 are kept lit. Thus, when the incidence limitation of the measurement light on the subject's eye 207 is released, a time period from turning-off of the light sources 201-1 to 201-3 to stable light emission is not necessary, and the control can be quickly performed. Similar effects can be obtained when the mirror or the filter is used.

The open/closed state of the shutters 291-1 to 291-3 is displayed on a shutter state display region 509 of a control software screen illustrated in FIG. 7 by the display control unit 112 described below. By displaying the open/closed state of the shutter, the examiner can clearly and easily understand which of the measurement light 206-1 to 206-3 is being applied to the subject's eye 207. Accordingly, certainty of an imaging operation can be improved.

<Wavelength of Each Light Source>

FIG. 4 illustrates an example of a wavelength distribution of the light sources used for the AOSLO unit, the WFSLO unit, the beacon unit, the fixation lamp unit, and the anterior eye portion observation unit. To enable the dichroic mirrors 270-1 to 270-4 to divide the light, different wavelength ranges are set thereto.

To reduce dazzling of the subject's eye, the light emitted from the light sources 201-1 to 201-4 are desirably infrared lights having wavelengths of 700 nm or more. The light source 201-3 of the beacon unit is required not to provide a high image quality, but to obtain a Hartmann image. Accordingly, a light amount can be smaller than those of the light sources 201-1 and 201-2. Thus, an influence of the wavelength of the light emitted from the light source 201-3 on the subject is relatively small even if the wavelength of the light is near a visible light region, and the wavelength of the light emitted from the light source 201-3 may be near the visible light region. Sensors normally used for the detectors 238-1 and 238-2 are silicon sensors. Since sensitivity of the silicon sensor is extremely low near 1000 nm, the wavelengths of the light emitted from the light sources 201-1 to 201-4 are desirably equal to or less than 1000 nm. The AOSLO apparatus 101 is configured to obtain an AOSLO image and uses a WFSLO image to assist obtaining of the desired AOSLO image. Thus, to ultimately obtain a desired AOSLO image with high resolution, the wavelength of the light emitted from the light source 201-1 is set shorter than that of the light emitted from the light source 201-2. As described above, the center wavelength of the light source 201-1 is desirably set near 840 nm based on eye characteristics.

It is therefore desirable that in the case of the AOSLO apparatus 101 for fundus observation, the beacon unit, the AOSLO unit, and the WFSLO unit are arranged in this order from the short wavelength side, and the respective center wavelengths are spaced from each other to facilitate separation by the dichroic mirrors.

An anterior eye portion image obtained by the light emitted from the anterior eye portion illumination light source 201-4 is used for initial alignment of the head unit 201. The alignment of the head unit 201 is performed while watching the WFSLO image. On the other hand, the light emitted from the light source 201-3 is used for measuring aberration necessary for obtaining the desired ultimate ALSO image with high resolution. Accordingly, since the light amount of the light source 201-3 is set larger than that of the anterior eye portion illumination light source 201-4 to accurately measure the aberration, by setting the wavelength of the light source 201-3 longer than that of the anterior eye portion illumination light source 201-4, the aberration can be accurately measured while reducing a burden on the subject. Further, since it is only necessary to obtain the anterior eye portion image used for the initial alignment of the head unit 201, the light amount of the anterior eye portion illumination light source 201-4 can be smaller than those of the other light sources. When the center wavelength of the anterior eye portion illumination light source 201-4 and the center wavelength of the light source 201-2 are switched, the center wavelength of the light source 201-2 that emits the light scanned on the subject's eye approaches the wavelength of the visible light. Consequently, the subject's eye follows a track of the light during scanning, and fixation may be unstable. Thus, the center wavelength of the anterior eye portion illumination light source 201-4 and the center wavelength of the light source 201-2 are under such conditions.

An interval between the center wavelengths is desirably double or more of the sum of ½ of full width at half maximum of adjacent light sources. According to the present exemplary embodiment, an interval between the center wavelengths of the light source 201-1 and the light source 201-2 is 80 nm, and an interval between the center wavelengths of the light source 201-1 and the light source 201-3 is also 80 nm. Full width at half maximum of the light sources 201-1 to 201-3 are respectively 50 nm, 20 nm, and 20 nm. Accordingly, double the sum of ½ of the full width at half maximum of the light source 201-1 and the light source 201-2 is 70 nm, double the sum of ½ of the full width at half maximum of the light source 201-1 and the light source 201-3 is also 70 nm, and the interval between the center wavelengths is set larger than these values. Thus, light losses at the respective light sources can be reduced as much as possible. Hereinbelow, a wavelength determination method including a wavelength determination step will be specifically described. When a wavelength distribution is generally Gaussian distribution, a width of the Gaussian distribution at a position of ½ of a peak (intensity peak) of the Gaussian distribution is referred to as full width at half maximum, and intensity at a position double the full width at half maximum is 1/16 of the peak value of the Gaussian distribution. In other words, 95% or more of the entire light amount is included in a portion where the width of the Gaussian distribution is less than double the full width at half maximum. Thus, by setting the interval between the center wavelengths double or more of the sum of ½ of full width at half maximum of the adjacent light sources as described above, overlapping of the wavelengths between the light sources can be made difficult. When the interval between the center wavelengths is set double ½ of full width at half maximum of the adjacent light sources, the interval between the center wavelengths can be reduced while preventing overlapping of the wavelengths between the light sources. Thus, the wavelengths can be effectively used. As a result, a wavelength as short as possible can be used to improve resolution.

In the above-described example, the interval between the center wavelengths is set double or more of the sum of ½ of full width at half maximum of the adjacent light sources. However, the interval is not limited to this. For example, the interval between the center wavelengths can be set "n" times or more of the sum of 1/n of full width at half maximum of the adjacent light sources, where "n" is a natural number. In the above-described example, "n" is 2. In other words, the interval between the center wavelengths is determined based on a value "n" times of the sum of 1/n of full width at half maximum of a plurality of adjacent measurement lights. (where "n" is a natural number.) More specifically, the interval between the center wavelengths is a value "n" times or more of the sum of 1/n of full width at half maximum of the plurality of adjacent measurement lights.

The wavelength width used for determining the interval between the center wavelengths may not be full width at half maximum. An arbitrary wavelength width can be used. For example, a wavelength width half of the full width at half maximum may be used from the start to omit the division described above, or a wavelength width near the full width of the wavelength may be used. In other words, the interval between the center wavelengths may be determined based on the respective wavelength widths of the plurality of adjacent measurement lights.

Further, when the interval between the center wavelengths is set double of the sum of ½ of full width at half maximum of the adjacent light sources, overlapping of the wavelengths between the light sources becomes greater than that when the interval between the center wavelengths is set greater than double of the sum of ½ of full width at half maximum of the adjacent light sources. In this case, an attenuation filter for attenuating the wavelengths at overlapping portion is disposed, and thus the influence of the wavelength overlapping can be reduced. For example, as the interval between the center wavelengths is narrower, the wavelength overlapping portion becomes larger. Thus, the attenuation filter for attenuating wavelengths of a wider range as the interval between the center wavelengths is narrower may be used. A table associating the interval between the center wavelengths with a range for attenuating the wavelength is prepared, and the control PC 106 inserts or remove the attenuation filter (not illustrated) into/from an arbitrary position of the optical path such as before the subject's eye 207 or each light source by referring to the table. The use of such an attenuation filter enables the center wavelengths to approach each other more, and the wavelengths can be more effectively used.

An interval between the center wavelength of the light source 201-3 and the center wavelength of the light source

201-4 may be determined or may not be determined by a method similar to the above-described method. The interval between the center wavelengths may not be determined because the anterior eye portion image does not need accuracy as high as the other images.

FIG. 4 illustrates a difference in wavelengths of the respective light sources, and it is not intended to define intensity or spectral shapes thereof.

<Image Formation>

Next, a configuration method of a captured image will be described.

The detector 238-1 converts the intensity of the entered light into a voltage. A voltage signal obtained at the detector 238-1 is converted into a digital value at an analog-digital (AD) board 276-1 in the control PC 106. The control PC 106 performs data processing in synchronization with an operation or a driving frequency of the XY scanner 219-1 to form an AOSLO image. A capturing speed of the AD board 276-1 is 15 MHz, for example. Similarly, a voltage signal obtained at the detector 238-2 is converted into a digital value at an AD board 276-2 in the control PC 106, and a WFSLO image is formed by the control PC 106.

A sampling frequency in a case where an image having a number of pixels N (pixels) is captured at a frame rate f (Hz) is f*N (Hz). To capture an image by reducing deterioration of signal intensity (desirably, without deteriorating the signal intensity), the sampling frequency needs to be smaller than a cutoff frequency fc (Hz) of the detector 238-1. This is represented by the following expression (1)

$$f*N<fc \qquad (1)$$

Based on the above expression (1), the frame rate f and the number of pixels N can be adjusted according to a purpose. In other words, a product of the frame rate and the number of pixels in combination stored in a storage unit is smaller than a cutoff frequency of a light receiving unit.

The sampling frequency is determined based on the cutoff frequency fc (Hz) of the detector 238-1. However, the frequency is not limited to this. For example, to surely prevent the signal intensity from deteriorating, a frequency lower than the cutoff frequency can be used as a reference. Alternatively, when the deterioration of the signal intensity can be permitted to a certain extent, a frequency higher than the cutoff frequency can be used as a reference. In other words, the frame rate and the number of pixels in combination stored in the storage unit are values determined based on frequency characteristics of the light receiving unit.

In the AOSLO apparatus according to the present exemplary embodiment, a frame rate can be selected by an imaging condition setting button 523 described below referring to FIG. 7. For example, the frame rate can be selected from 32 Hz, 64 Hz, and 120 Hz. For the number of pixels, the number of vertical pixels is fixed at 400 pixels, while the numbers of horizontal pixels are respectively 400 pixels at the frame rate of 32 Hz, 200 pixels at the frame rate of 64 Hz, and 100 pixels at the frame rate of 120 Hz. The frame rates are not limited to these values, and other values can be employed. In addition, the numbers of pixels are also not limited to the above values, and other values can be employed. It is described that the number of vertical pixels is fixed at 400 pixels. However, not limited to this, the number of horizontal pixels may be fixed. The frame rate and the number of pixels are not limited to the above combination, and other combinations of values can be employed.

When the cutoff frequency of the detector 238-1 is, for example, 15 MHz, the following combinations of frame rates and pixels are determined to satisfy the condition of the expression (1):

$$32*400*400=5{,}120{,}000<15{,}000{,}000$$

$$64*400*200=5{,}120{,}000<15{,}000{,}000$$

$$120*400*100=4{,}800{,}000<15{,}000{,}000$$

Determining such options can avoid combinations that cause reduction of signal intensity.

<Control PC 106>

Figure 5:
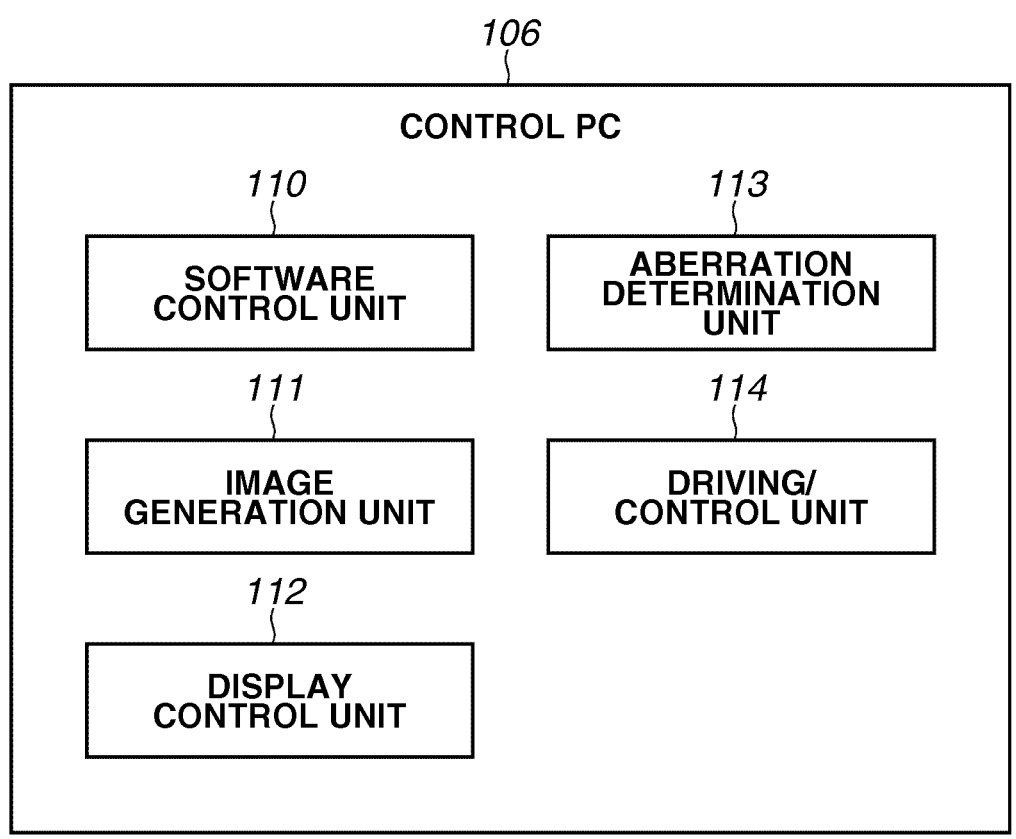
FIG. 5 schematically illustrates an example of a function of a control personal computer (PC).

An example of functions of the control PC 106 will be described. FIG. 5 schematically illustrates the example of the functions of the control PC 106.

The control PC 106 functions as a software control unit 110, an image generation unit 111, a display control unit 112, an aberration determination unit 113, and a driving/control unit 114 by executing a predetermined program stored in a storage device such as a memory by a processing unit such as a central processing unit (CPU).

The software control unit 110 controls activation or stopping of measurement control software and viewer software. For example, the software control unit 110 activates the measurement control software when power of the AOSLO apparatus 101 is turned on or when an examiner specifies an execution file of the control software. The software control unit 110 activates the viewer software when the examiner specifies an execution file of the viewer software. Further, the software control unit 110 stops the measurement control software and the viewer software when the examiner instructs an end of the software. The control software and the viewer software may be stored in a storage unit such as a memory included in the control PC 106, or in an external storage unit communicable with the control PC 106 by wireless or wire.

The image generation unit 111 generates various images. For example, the image generation unit 111 generates an AOSLO image based on an output of the AD board 276-1. In other words, the image generation unit 111 corresponds to an example of an obtaining unit for obtaining the image at a frame rate and the number of pixels of one combination among a plurality of combinations using the aberration-corrected return light from the subject's eye. The image generation unit 111 generates a WFSLO image based on an output of the AD board 276-2. The image generation unit 111 generates a Hartmann image based on an output of the wavefront sensor 255. The image generation unit 111 generates an anterior eye portion image based on an output of the CCD camera 260.

The display control unit 112 displays various pieces of information such as the images generated by the image generation unit 111 on the liquid crystal monitor 105. The display control unit displays a graph or values of aberrations determined by the aberration determination unit 113 on the liquid crystal monitor 105.

The display control unit 112 further displays open/closed states of the shutters 291-1 to 291-3 in a shutter state display region 509.

The information to be displayed in the shutter state display region 509 is not limited to the shutter open/closed state. For example, any information indicating the incident state of the measurement light on the subject's eye can be used. Information indicating insertion or removal of a filter in/from the optical path may be displayed when the filter is used in place of the shutter, or information indicating incidence of the measurement light may be displayed.

The aberration determination unit 113 determines aberration at the subject's eye 207 based on an output of the wavefront sensor 255. More specifically, the aberration determination unit 113 determines aberration at the subject's eye 207 based on the Hartmann image.

The driving/control unit 114 drives various movable members. More specifically, the driving/control unit 114 drives the XY scanners 219-1 and 219-2 via the optical scanner driver 282. In other words, the driving/control unit 114 corresponds to an example of a control unit for controlling a scanning unit to obtain an image at a frame rate of one combination among the plurality of combinations. The driving/control unit 114 also drives the electric stages 217-1 to 217-4 via the electric stage driver 283.

Further, the driving/control unit 114 drives the fixation lamp 256 via the fixation lamp driver 284. More specifically, the driving/control unit 114 controls movement of a lighting position 265, switching between lighting and flashing, and changing of a size or a shape. The driving/control unit 114 controls the spatial light modulator 259 via the spatial light modulator driver 288. Specifically, the driving/control unit 114 controls the spatial light modulator 259 based on the aberration determined by the aberration determination unit 113, and corrects the aberration at the subject's eye. More specifically, the driving/control unit 114 controls the spatial light modulator 259 to reduce the aberration.

Further, the driving/control unit 114 drives the chin rest 108 via the chin rest driving unit 109 according to an examiner's input.

The driving/control unit 114 controls opening/closing of the shutters 291-1 to 291-3. Further, the driving/control unit 114 controls turning on or off the light source.

<Imaging Procedure>

Figure 6:
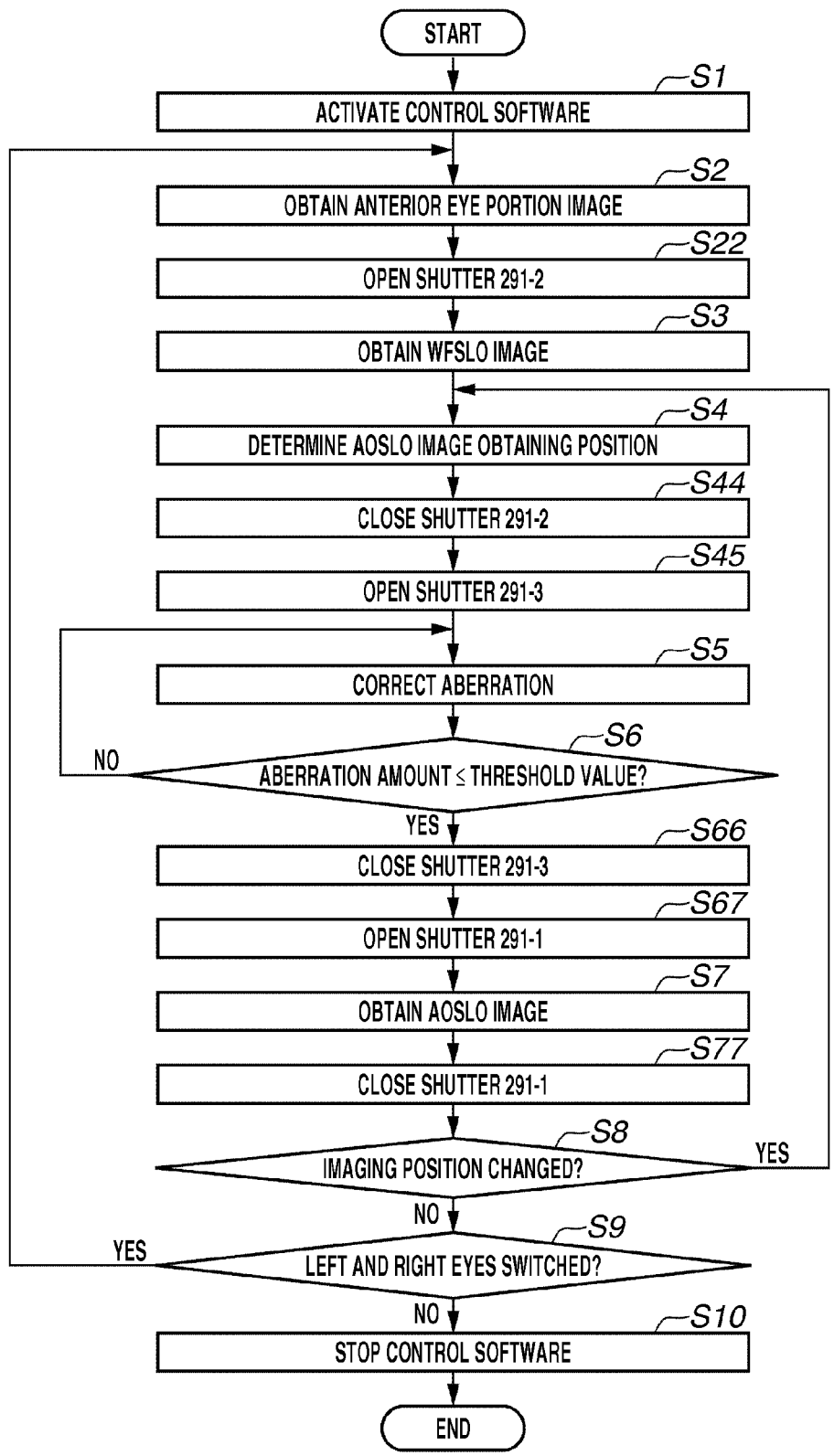
FIG. 6 is a flowchart illustrating an example of an imaging procedure performed by the AOSLO apparatus according to the exemplary embodiment of the present invention.

Next, referring to FIGS. 6 and 7, an imaging procedure performed in the AOSLO apparatus 101 of the present exemplary embodiment will be described. FIG. 6 is a flowchart illustrating an example of an operation of the AOSLO apparatus according to the exemplary embodiment. FIG. 7 illustrates an example of a control screen of the AOSLO apparatus 101 displayed on the liquid crystal monitor 105 according to the exemplary embodiment.

Hereinbelow, each step of the flowchart will be described in detail. In an initial state, it is assumed that the shutters 291-1 to 291-3 are all closed.

When power is turned on for the AOSLO apparatus 101 including the control PC 106, each processing of the AOSLO apparatus 101 is started.

[Step S1]

When power is turned on for the AOSLO apparatus 101 including the control PC 106, the software control unit 110 activates the measurement control software. When the measurement control software is activated, the display control unit 112 displays the control software screen illustrated in FIG. 7 on the liquid crystal monitor 105. The subject sets a face on the face rest member 104 after the measurement control software has been activated.

An example of the control screen illustrated in FIG. 7 will be described. A screen configuration of the control software illustrated in FIG. 7 is only an example, and thus in no way limitative. In other words, arrangement or the like of the control screen can be arbitrarily changed.

Figure 7:
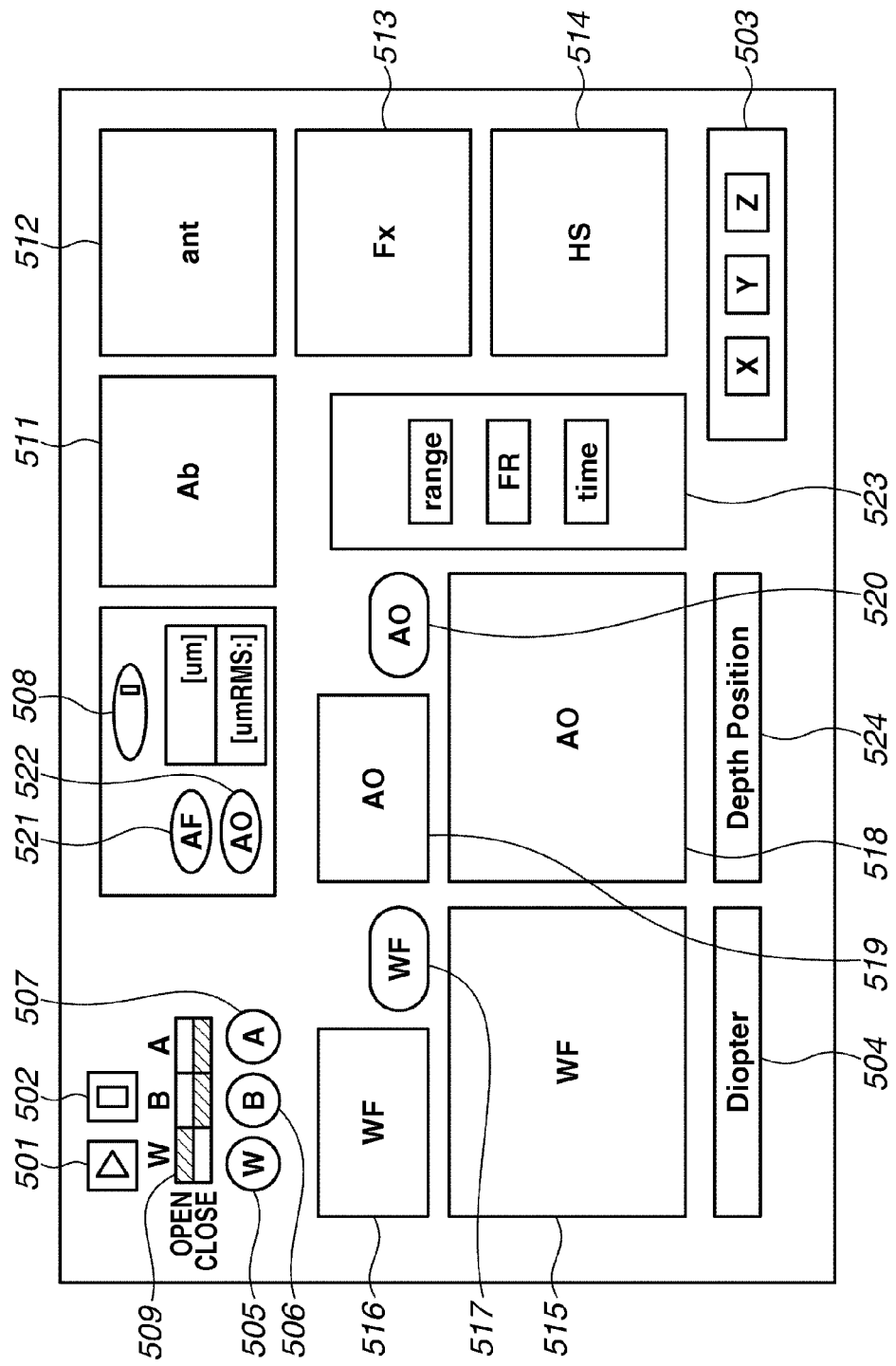
FIG. 7 illustrates an example of a configuration of a control software screen of the AOSLO apparatus according to the exemplary embodiment of the present invention.

The control screen illustrated in FIG. 7 includes an execution button 501, a stop button 502, an electric stage button 503, a focus adjustment button 504, a WFSLO measurement button 505, an aberration measurement button 506, and an AOSLO measurement button 507.

The control screen illustrated in FIG. 7 further includes an aberration correction temporary stop button 508, a shutter state display region 509, an aberration display region 511, an anterior eye portion display region 512, a fixation lamp position display region 513, a wavefront display region 514, and a WFSLO display region 515.

The control screen illustrated in FIG. 7 further includes a WFSLO intensity display region 516, a WFSLO recording button 517, an AOSLO display region 518, an AOSLO intensity display region 519, an AOSLO recording button 520, and an autofocus button 521.

The control screen illustrated in FIG. 7 further includes an aberration correction button 522, an imaging condition setting button 523, and a depth adjustment button 524.

When the execution button 501 is selected (e.g., clicked) by an instruction unit such as a mouse, then, the driving/control unit 114 lights the anterior eye portion illumination light source 201-4, and the light emitted from the anterior eye portion illumination light source 201-4 enters into the subject's eye 207. Then, the display control unit 112 displays an anterior eye portion image generated based on an output of the CCD camera 260 in the anterior eye portion display region 512.

When the execution button 501 is selected, the control PC 106 may display a screen for selecting or registering patient information on the liquid crystal monitor 105. In this case, after the patient information is selected or registered, the anterior eye portion illumination light source 201-4 can be lit, and the display control unit 112 can display the anterior eye portion image in the anterior eye portion display region 512. The selection by the instruction unit is not limited to clicking. In the case where the liquid crystal monitor 105 has a touch panel function, the examiner can perform selection by touching the monitor.

When the stop button 502 is selected, the software control unit 110 stops the control software.

The electric stage movement button 503 includes an X stage movement button, a Y stage movement button, and a Z stage movement button. When the electric stage movement button 503 is selected, the driving/control unit 114 moves the chin rest 108 via the chin rest driving unit 109. For example, each of the X stage movement button, the Y stage movement button, and the Z stage movement button is a slider, and the driving/control unit 114 moves the chin rest 108 according to a movement amount and a movement direction of the slider. For example, when the Y stage button is selected, the driving/control unit 114 moves the chin rest 108 in the Y direction. Similarly, the driving/control unit 114 moves the chin rest 108 in the X direction and the Z direction according to the selected buttons. The electric stage movement button 503 is not limited to the slider. Any other form can be employed as long as an instruction to move the chin rest 108 can be issued.

For example, the focus adjustment button 504 is a slider. The driving/control unit 114 drives the lenses 235-10, 235-14, 235-16, and 235-18 according to a movement amount and a movement direction of the slider. The focus adjustment button 504 is not limited to the slider. Any other form can be employed as long an instruction to move the lenses 235-10, 235-14, 235-16, and 235-18 can be issued.

When the WFSLO measurement button 505 is selected, the control PC 106 permits the light emitted from the light source 201-1 to enter into the subject's eye. More specifically, a state in which entry of the light emitted from the light sources 201-1 to 201-3 into the subject's eye is limited before selection of the WFSLO measurement button 505 is changed to a state in which the light emitted from the light source 201-2 enters into the subject's eye. This switching is carried out by, for example, lighting the turned-off light source 201-2 or retreating the shutter inserted into the optical path connecting the subject's eye with the light source 201-2 by the driving/control unit 114.

When the aberration measurement button 506 is selected, the driving/control unit 114 limits entry of the light emitted from the light source 201-2 into the subject's eye. The entry of the emitted light into the subject's eye 207 is limited by, for example, closing the shutter 291-2 on the optical path connecting the subject's eye 207 with the light source 201-2 or turning off the light source 201-2. When the aberration measurement button 506 is selected, the control PC 106 permits the light emitted from the light source 201-3 to enter into the subject's eye 207.

More specifically, a state in which entry of the light emitted from the light sources 201-1 and 201-3 into the subject's eye is limited before the aberration measurement button 506 is selected is changed to a state in which the light emitted from the light source 201-3 enters into the subject's eye. This switching is carried out by, for example, lighting the turned-off light source 201-3 or opening the shutter 291-3 inserted into the optical path connecting the subject's eye 207 with the light source 201-3 by the driving/control unit 114. Either one of a timing of the limitation of the entry of the light emitted from the light source 201-2 into the subject's eye 207 and a timing of the permission of the entry of the light emitted from the light source 201-3 into the subject's eye 207 can be first, or both can be simultaneously executed. However, it is desirable that to control the increase of a light amount entered into the subject's eye 207 to a minimum, the entry of the light emitted from the light source 201-3 into the subject's eye 207 is permitted after the entry of the light emitted from the light source 201-2 into the subject's eye 207 is limited.

When the AOSLO measurement button 507 is selected, the driving/control unit 114 limits entry of the light emitted from the light source 201-3 into the subject's eye. The entry of the emitted light into the subject's eye 207 is limited by, for example, closing the shutter 291-3 on the optical path connecting the subject's eye 207 with the light source 201-3 or turning off the light source 201-3. When the AOSLO measurement button 507 is selected, the control PC 106 permits the light emitted from the light source 201-1 to enter into the subject's eye 207.

More specifically, a state in which entry of the lights emitted from the light sources 201-1 and 201-2 into the subject's eye 207 is limited before the AOSLO measurement button 507 is selected is changed to a state in which the light emitted from the light source 201-1 enters into the subject's eye 207. This switching is carried out by, for example, lighting the turned-off light source 201-1 or opening the shutter 291-1 inserted into the optical path connecting the subject's eye 207 with the light source 201-1 by the driving/control unit 114. Either one of a timing the limitation of the entry of the light emitted from the light source 201-3 into the subject's eye 207 and a timing of the permission of the entry of the light emitted from the light source 201-1 into the subject's eye 207 can be first, or both can be simultaneously executed. However, it is desirable that to control the increase of a light amount entered into the subject's eye 207 to a minimum, the entry of the light emitted from the light source 201-1 into the subject's eye 207 is permitted after the entry of the light emitted from the light source 201-3 into the subject's eye 207 is limited.

When the aberration correction temporary stop button 508 is selected, the control PC 106 temporarily stops aberration correction. For example, while the aberration determination unit 113 continues aberration calculation, the control of the spatial light modulator 259 by the driving/control unit 114 is stopped. Alternatively, the aberration calculation itself is stopped. A resume button (not illustrated) may be disposed, and the aberration correction may be resumed when the resume button is selected. Alternatively, when the aberration correction temporary stop button 508 is selected again, the aberration correction may be resumed.

In the shutter state display region 509, information indicating open/closed states of the shutters 291-1 to 291-3 is displayed by the display control unit 112. In the example illustrated in FIG. 7, for the respective shutters 291-1 to 291-3, regions indicating an open state (OPEN in the drawing) and a closed state (CLOSE in the drawing) of the shutter are provided. The regions are highlighted according to the open/closed states of the shutters 291-1 to 291-3. For example, FIG. 7 illustrates the open state of the shutter 291-1 and the closed states of the shutters 291-2 and 291-3. However, the form of the shutter state display region 509 is not limited to this example. Any other display forms can be employed as long as the open/closed states of the shutters 291-1 to 291-3 can be confirmed. For example, switches corresponding to the respective shutters 291-1 to 291-3 can be displayed. In this case, the switch is pressed when the shutter is opened while the switch is not pressed when the shutter is closed.

In the aberration display region 511, the aberration determined (calculated) by the aberration determination unit 113 is displayed as a time-series graph by the display control unit 112.

In the anterior eye portion display region 512, the anterior eye portion image generated by image generation unit 111 based on the output of the CCD camera 260 is displayed by the display control unit 112.

In the fixation lamp position display region 513, information indicating a fixation position is displayed by the display control unit 112. For example, in the fixation lamp position display region 513, a grid indicating fixation coordinates is displayed, and the fixation position is displayed as a bright spot on the grid. When the operation unit selects a certain point on the grid, the driving/control unit 114 changes a lighting position 265 of the fixation lamp 256 according to the selected position. In the fixation lamp position display region 513, coordinates indicating a current fixation position may be displayed as numerical values. In this case, the lighting position 265 can be changed by changing the displayed numerical values.

In the wavefront display region 514, a Hartmann image detected by the wavefront sensor 255 is displayed by the display control unit 112. The wavefront display region 514 may be always disposed, or popped up as another window when the aberration measurement button 506 is selected, aberration measurement is started, and a Hartmann image is obtained. The pop-up configuration enables the screen of the liquid crystal monitor 105 to be effectively used in a state of not measuring aberration.

In the WFSLO display region 515, a WFSLO image generated by the image generation unit 111 is displayed by the display control unit 112.

In the WFSLO intensity display region 516, signal intensity of the WFSLO image is displayed by the display control unit 112. More specifically, the signal intensity of the WFSLO image is displayed as a time-series graph.

When the WFSLO recording button 517 is selected, the driving/control unit 114 records the WFSLO image in a storage unit (not illustrated) such as a hard disk drive (HDD).

In the AOSLO display region 518, an aberration-corrected AOSLO image is displayed by the display control unit 112.

In the AOSLO intensity display region 519, signal intensity of the AOSLO image is displayed by the display control unit 112. More specifically, the signal intensity of the AOSLO image is displayed as a time-series graph.

When the AOSLO recording button 520 is selected, the driving/control unit 114 records the AOSLO image in the storage unit (not illustrated) such as a HDD.

When the autofocus button 521 is selected, in the driving/control unit 114, positions of the lenses 235-10, 235-14, 235-16, and 235-18 are automatically adjusted so that a defocus value can be small.

When the aberration correction button 522 is selected, in the driving/control unit 114, the spatial light modulator 259 is automatically adjusted so that an aberration amount can be smaller.

The imaging condition setting button 523 includes, for example, an imaging field angle setting button, a frame rate setting button, and an imaging time setting button. For example, the imaging field angle setting button includes a plurality of buttons corresponding to a plurality of field angles. The examiner can perform imaging with a desired filed angle by selecting a button corresponding to the desired field angle. The frame rate setting button and the imaging time setting button are configured as in the case of the imaging field angle setting button. For example, by selecting one corresponding to a desired frame rate among the plurality of frame rate setting buttons, a field angle correspond to the frame rate is selected. For example, the field angle indicates the number of pixels. As the number of pixels is smaller, the field angle is narrower. By selecting one corresponding to a desired field angle among the plurality of imaging field angle setting buttons, a frame rate corresponding to the field angle (number of pixels) is selected.

Figure 8:
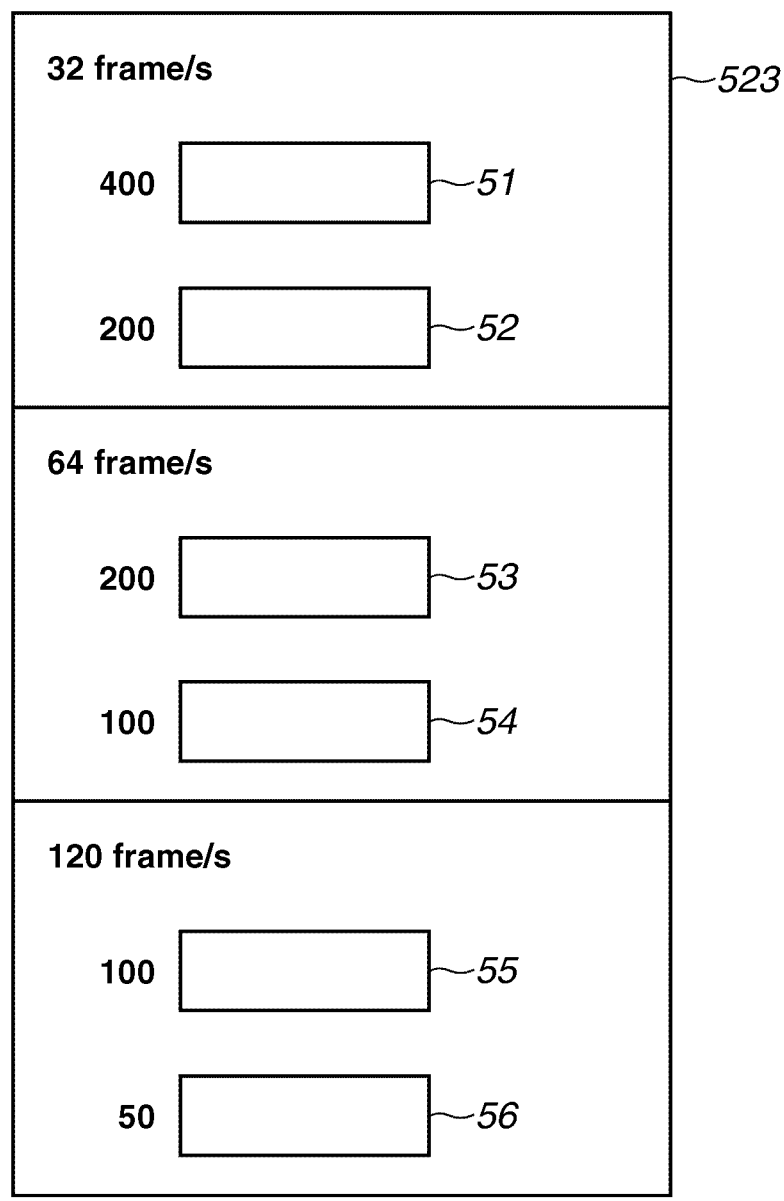
FIG. 8 illustrates an example of an imaging condition setting button according to the exemplary embodiment of the present invention.

As the imaging condition setting buttons 523, there is no need to separately arrange the imaging field angle setting button and the frame rate setting button. For example, a combination of one frame rate with the number of pixels can be provided as one button. In this case, a plurality of buttons may be provided for different combinations. FIG. 8 illustrates such an example.

A combination of a frame rate with the number of pixels is allocated to each of buttons 51 to 56. The combination of the frame rate with the number of pixels is stored in a memory or the like included in the control PC 106. In other words, the memory included in the control PC 106 corresponds to an example of a storage unit for storing a plurality of combinations of frame rates for obtaining an image of the subject's eye with numbers of pixels of the image according to frame rate values.

For example, a combination of a frame rate 32 Hz with the number of horizontal pixels 400 is allocated to the button 51, and a combination of a frame rate 32 Hz with the number of horizontal pixels 200 is allocated to the button 52. A combination of a frame rate 64 Hz with the number of horizontal pixels 200 is allocated to the button 53, and a combination of a frame rate 64 Hz with the number of horizontal pixels 100 is allocated to the button 54. A combination of a frame rate 120 Hz with the number of horizontal pixels 100 is allocated to the button 55, and a combination of a frame rate 120 Hz with the number of horizontal pixels 50 is allocated to the button 56. The number of buttons arranged for each frame rate is not limited to two. In addition, the numbers of buttons to be arranged for the respective frame rates are not all uniformly two.

The buttons 51 to 56 are displayed by the display control unit 112. In other words, the display control unit 112 corresponds to an example of a display control unit for causing a plurality of display units to display display forms indicating combinations according to frame rate values. The AOSLO apparatus 101 obtains an AOSLO image based on the frame rates and the numbers pixels specified by the buttons 51 to 56. In other words, the image generation unit 111 which is an example of an obtaining unit obtains an image based on a frame rate and the number of pixels in a combination indicated by one display form selected from among the plurality of display forms displayed by the display unit.

For simplicity, the imaging time setting button is not illustrated in FIG. 8. In FIG. 8, the numbers of horizontal pixels are displayed beside the respective buttons 51 to 56. However, the arrangement is not limited to this. For example, not the number of pixels but symbols such as "S" or "L" can be displayed according to sizes of the numbers of pixels at the respective frame rate. For example, "L" may be displayed beside the button 51, and "S" may be displayed beside the button 52.

The control screen can further include button for selecting measurement purposes. For example, the control screen includes a blood flow measurement button and a visual cell measurement button. In blood flow measurement, a blood flow rate can be highly accurately measured by using a relatively high frame rate. Thus, when the blood flow measurement button is selected, the buttons 51 and 52 of the frame rate of 32 frames/s cannot be selected. Display indicating that the buttons 51 and 52 cannot be selected is performed by, for example, hiding the buttons 51 and 52.

In measurement of a visual cell distribution, a value of a speed of a frame rate higher than that a value of a speed of a frame rate in the blood flow measurement cannot be required. A larger number of pixels is desirable to obtain a useful visual cell distribution. Thus, when the visual cell measurement button is selected, only the button 51 where the number of pixels is large is selected to obtain a useful visual cell distribution. Display indicating that the buttons 52 to 56 cannot be selected is performed by, for example, hiding the buttons 52 to 56. In addition, not only the button 51 but also the buttons 52 and 53 may be displayed in a selectable manner, or only the buttons 51 and 52 of relatively low frame rates of 32 frames/s may be displayed in a selectable manner. In other words, the display control unit 112 disables selection of at least one of a plurality of display forms displayed by the display unit according to a measurement type for the subject's eye. The apparatus can employ a configuration in which a frame rate or the like suitable for a measurement purpose is automatically determined according to selection of the visual cell measurement button or the blood flow measurement button.

Such a configuration enables sure selection of a frame rate or the like appropriate for the measurement purpose without any mistakes. Thus, re-measurement rarely happens, and burdens on the subject can be reduced.

When the visual cell measurement button is selected, visual cell analysis may be automatically performed for an obtained image. For example, processing for detecting a visual cell from the obtained image is performed. Further, Voronoi analysis or visual cell density calculation can be performed for the detected visual cell. On the other hand, when the blood flow measurement button is selected, blood flow rate analysis may be automatically performed for the obtained image. For example, blood cells are detected from the obtained image, and a blood flow rate is calculated based on a movement amount of the blood cells. As described above, image processing suitable for a measurement purpose is performed on the image after the measurement according to which of the visual cell measurement button and the blood flow measurement button has been pressed.

The depth adjustment button 524 is, for example, a slider. The driving/control unit 114 drives the lens 235-10 according to a movement amount and a movement direction of the slider. The depth adjustment button 524 is not limited to the slider. Any other forms can be employed as long as the lens 235-10 can be driven.

In the aberration display region 525, an aberration amount of a defocus component (μm) and all aberration amounts (μm RMS) determined by the aberration determination unit 113 are displayed by the display control unit 112. Only one of these two amounts may be displayed. The units of the displayed aberration amounts are not limited to the above units, and other units can be used.

Hereinbelow, description will return to the processing in the flowchart of FIG. 6.

[Step S2]

When the execution button 501 on the control software screen is pressed, an image of the anterior eye portion is displayed in the anterior eye portion display region 512. In a case where a center of a pupil is not correctly displayed at a screen center, the head portion 102 is moved to a roughly correct position using the joy stick 107. When further adjustment is necessary, the electric stage button 503 on the control screen is pressed, and the chin rest 108 is slightly moved by the driving/control unit 114.

[Step S22]

Then, the driving/control unit 114 opens the closed WFSLO shutter 291-2. In the shutter state display region 509, the open state of the WFSLO shutter 291-2 is displayed. In the shutter state display region 509, the closed states of the shutters 291-1 and 291-3 are also displayed.

Timing of opening the WFSLO shutter 291-2 may be when the execution button 501 on the control software screen is selected, when the control software is activated, or before the image of the anterior eye portion is displayed in the anterior eye portion display region 512.

[Step S3]

When the image of the anterior eye portion is displayed in a roughly correct state, a WFSLO image is displayed in the WFSLO display region 515. For example, the examiner sets the fixation lamp at a center position of the fixation lamp position display region 513, and guides a line of sight of the subject's eye 207 to the center. For example, the WFSLO measurement button 505 is automatically selected when the control software is activated or when the execution button 501 is selected.

Then, watching intensity of the WFSLO image displayed in the WFSLO intensity display region 516, the examiner adjusts the focus adjustment button 504 to increase the WFSLO intensity. In the WFSLO intensity display region 516, signal intensity detected by the WFSLO unit is displayed in the chronological order with a horizontal axis indicating time and a vertical axis indicating signal intensity. By adjusting the focus adjustment button 504, the positions of the lenses 235-10, 235-14, 235-16, and 235-18 are simultaneously adjusted by the driving/control unit 114.

When the WFSLO image is clearly displayed, the examiner presses the WFSLO recording button 517 to store WFSLO data (WFSLO image).

[Step S4]

The examiner checks the WFSLO image displayed in the WFSLO display region 515 and stored in step S3, and determines a position for obtaining an AOSLO image using means described below. Then, the examiner guides the line of sight of the subject's eye 207 so that the position can be set, for example, on the center of the WFSLO display region 515.

There are two means for determining the position for obtaining the AOSLO image: one is a method for instructing a position of the fixation lamp in the fixation lamp position display region 513, and the other is a method for clicking a desired position of the WFSLO image in the WFSLO image display region 515. A pixel in the WFSLO display region 515 and the position of the fixation lamp are associated with each other. The driving/control unit 114 automatically moves the position of the fixation lamp according to the clicked position to guide the line of sight of the subject's eye to a desired position. Since the line of sight of the subject's eye is guided using the WFSLO image stored in step S3, it is not necessary to enter the light emitted from the light source 201-2 for obtaining the WFSLO image into the subject's eye during the processing in step S4.

After confirmation that the position for obtaining the AOSLO image has moved to the center of the WFSLO display region 515, the processing proceeds to a next step. According to the present exemplary embodiment, the region where the AOSLO image is obtained is a rectangular region of a predetermined size around the optical axis of the optical system illustrated in FIG. 2. In other words, the region where the AOSLO image is obtained is a rectangular region of a predetermined size around the center of the WFSLO display region 515. The region where the AOSLO image is obtained is not limited to this, and can be arbitrarily changed.

The WFSLO image may be obtained again after the position of the fixation lamp has been changed, and whether the desired position of the subject's eye 207 is at the center position of the WFSLO display region 515 may be confirmed to adjust the fixation position again. In this case, when entry of the measurement light from the light source 201-3 into the subject's eye 207 is limited, the limitation is released to enter the measurement light into the subject's eye 207. Thus, the desired position of the subject's eye 207 can be surely moved to the center position of the WFSLO display region 515, and illuminating time of the light to the subject's eye 207 can be shortened.

[Step S44]

When the aberration measurement button 506 is selected, the driving/control unit 114 closes the shutter 291-2. Closing the shutter 291-2 limits (blocks off) entry of the light emitted from the light source 201-2 into the subject's eye 207. In response to the storage of the WFSLO image, the driving/control unit 114 can close the shutter 291-2. In other words, the processing in step S44 can be carried out before the processing in step S4.

[Step S45]

Then, the driving/control unit 114 opens the shutter 291-3. Opening the shutter 291-3 enables the light emitted from the light source 201-3 to enter into the subject's eye 207. For example, the fixation lamp 256 is in a lit state when the control software is activated or the execution button 501 is selected.

In the shutter state display region 509, the open state of the shutter 291-3 is displayed, and the closed states of the shutters 291-1 and 291-2 are displayed.

[Steps S5 and S6]

Then, the display control unit 112 displays a Hartmann image detected by the wavefront sensor 255 in the wavefront display region 514. The display control unit 112 displays aberration calculated from the Harman image in the aberration display region 511. The aberration is displayed by being divided into a defocus component (μm) and all aberration amounts (μm RAM). Since the positions of the focus lenses 235-10 and 235-16 of the AOSLO measurement light and the beacon light have been adjusted in step S3, it is in a state that aberration measurement can be performed in step S5.

When the autofocus button 521 is pressed, the driving/control unit 114 automatically adjusts the positions of the lenses 235-10, 235-14, 235-16, and 235-18 to reduce a defocus value.

Then, when the aberration correction button 522 is pressed, the driving/control unit 114 automatically adjusts the spatial light modulator 259 in a direction where an aberration amount is smaller. In addition, the display control unit 112 displays a value of the aberration amount in real time on the liquid crystal monitor 105. The driving/control unit 114 compares the aberration amount with a predetermined threshold value. When the value of the aberration amount is equal to or lower than a predetermined threshold value (for example, 0.03 μm RMS) (YES in step S6), the driving/control unit 114 automatically presses the AOSLO measurement button 507, and the processing proceeds to a next step. When the value of the aberration amount is not equal to or lower than the predetermined threshold value (NO in step S6), the examiner can press the aberration correction temporary stop button 508 to stop the aberration correction. Then, the processing may proceed to a next step by pressing the AOSLO measurement button 507. The threshold value of the aberration amount is not limited to the above value, and can be arbitrarily set. When the aberration amount calculated by the aberration determination unit 113 is not equal to or lower than the predetermined threshold value for a predetermined time, the AOSLO measurement button 507 may be automatically selected by the driving/control unit 114.

[Step S66]

When the value of the aberration amount is equal to or lower than the predetermined threshold value, the driving/control unit 114 closes the shutter 291-3. In other words, when the AOSLO measurement button 507 is selected, the driving/control unit 114 closes the shutter 291-3. Closing the shutter 291-3 limits (blocks off) entry of the light emitted from the light source 201-3 into the subject's eye 207.

[Step S67]

When the shutter 291-3 is closed, the driving/control unit 114 opens the shutter 291-1. In other words, when the AOSLO measurement button 507 is selected, the driving/control unit 114 opens the shutter 291-1. Opening the shutter 291-1 enables the light emitted from the light source 201-1 to enter into the subject's eye 207. In the shutter state display region 509, the open state of the shutter 291-1 is displayed, and the closed states of the shutters 291-2 and 291-3 are displayed.

[Step S7]

An aberration-corrected AOSLO image is displayed in the AOSLO display region 518. In the AOSLO intensity display region 519, as in the case of the WFSLO intensity display region 516, signal intensity of the AOSLO image is displayed in the chronological order.

When the signal intensity is insufficient, the examiner adjusts a focus and a chin rest position to increase the signal intensity while watching the AOSLO intensity display region 519.

The examiner can designate an imaging field angle, a frame rate, and imaging time by the imaging condition setting button 523. It is desirable that a frame rate is set to 342 Hz when the visual cell distribution is measured, and to 64 Hz or 120 Hz when the blood flow rate is measured.

The examiner can also adjust an imaging range of the subject's eye 207 in the depth direction by adjusting the depth adjustment button 524 to move the lens 235-10. More specifically, by adjusting the depth adjustment button 524, an image of a desired layer such as a visual cell layer, a nerve fiber layer or a pigment epithelial layer can be obtained.

When the AOSLO image is clearly displayed, the examiner presses the AOSLO recording button 520 to store AOSLO data (AOSLO image). Then, the driving/control unit 114 limits entry of the measurement light 206-1 into the subject's eye 207.

[Step S77]

After the AOSLO image is stored, the AOSLO shutter 291-1 is closed to limit entry of the measurement light 206-1 into the subject's eye. In the shutter state display region 509, closed states of all the shutters 291-1 to 291-3 are displayed.

[Step S8]

The examiner determines whether to change the imaging position. When the imaging position is changed (YES in step S8), the processing returns to step S4. The processing in Step S44 after the return to step S4 is omitted. On the other hand, when the imaging position is not changed (NO in step S8), the processing proceeds to a next step. Supposing that an imaging position changing button is displayed on the liquid crystal display monitor 105, when the imaging position changing button is selected, the control PC 106 may determine that the imaging position will be changed. When the imaging position changing button is not selected for a predetermined time after the AOSLO image has been stored, the control PC 106 may determine that the imaging position will not be changed.

[Step S9]

The examiner determines whether to switch left and right eyes. When the switching is carried out (YES in step S9), the processing returns to step S2. On the other hand, when the left and right eyes are switched (NO in step S9), the processing proceeds to a next step. Supposing that a left and right eye switching button is displayed on the liquid crystal display monitor 105, when the left and right eye switching button is selected, the control PC 106 may determine that an eye to be examined will be switched. When the left and right eye switching button is not selected for a predetermined time after the AOSLO image has been stored, the control PC 106 may determine that an eye to be examined will not be switched.

The execution order of the processing in step S8 and step S9 can be reversed.

[Step S10]

The examiner presses the stop button 502 to stop the control software. The control software is stopped, and the series of imaging operations is ended.

<Image Confirmation>

Figure 9:
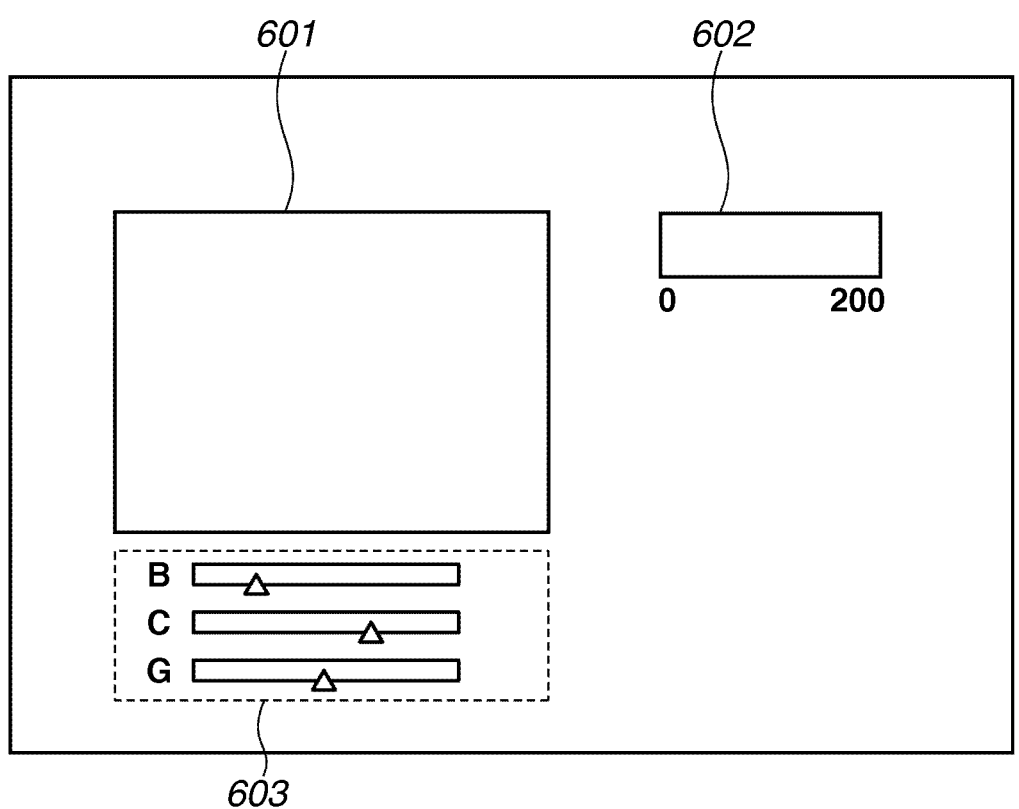
FIG. 9 illustrates an example of a configuration of an image browsing software screen of the AOSLO apparatus according to the exemplary embodiment of the present invention.

Next, referring to FIG. 9, a method for forming data of a captured image into an image to confirm the data by the AOSLO apparatus 101 according to the present exemplary embodiment will be described. FIG. 9 illustrates an example of a configuration of an image browsing software screen according to the present exemplary embodiment.

When viewer software for visualizing captured image data is activated by the software control unit 110, the display control unit 112 displays the image browsing software screen illustrated in FIG. 9 in the liquid crystal monitor 105.

The viewer software can read the stored WFSLO data or AOSLO data to form an image.

The viewer software screen includes an image display region 601, an image number selection unit 602, and an image quality adjustment unit 603.

In the image display region 601, an image selected using the image number selection unit 602, such as an AOSLO image, is displayed. A WFSLO image corresponding to the AOSLO image can be displayed in the image display region 601 by providing a display switching unit such as a tab. Accordingly, the AOSLO image and the WFSLO image can be easily compared with each other in sight. The AOSLO image and the WFSLO image may be displayed side by side.

The image number selection unit 602 is configured to select a desired AOSLO image from a plurality of AOSLO images obtained by the AOSLO apparatus 101. For example, the image number selection unit 602 is a slider. A position of the slider is associated with an image number of the AOSLO image. The examiner can select a desired AOSLO image by moving the slider via an instruction unit. The number of captured images varies depending on measuring time, and image numbers are assigned to the images in chronological order. The image number selection unit 602 is not limited to the slider. A region to which the image number can be directly input may be employed.

The image quality adjustment unit 603 is a slider configured to adjust image brightness, contrast, and gamma ("B", "C", and "G"). Image quality can be adjusted by sliding the slider left and right. The control PC 106 adjusts image quality of an AOSLO image and the like based on an input to the image quality adjustment unit 603.

The viewer software screen is not limited to the above example. For example, a fixation position when the AOSLO image displayed in the image display region 601 is obtained may be displayed as a coordinate value or a drawing. Coordinates of the face rest member 104 when the AOSLO image displayed in the image display region 601 is obtained can be displayed. Further, luminance or amplitude of the AOSLO image with respect to scanning time when the AOSLO image displayed in the image display region 601 is obtained may be displayed as a graph. Information indicating a position of at least one of the lenses 235-10, 235-14, 235-16, and 235-18 when the AOSLO image displayed in the image display region 601 is obtained can be displayed.

An AOSLO image can be displayed as a moving image in the image display region 601. In this case, for parameters such as the fixation position at the time of obtaining the AOSLO image, values corresponding to the AOSLO image are sequentially displayed.

As described above, according to the present exemplary embodiment, the plurality of combinations of frame rates with the numbers of pixels is prepared, and the AOSLO image is obtained based on the frame rate and the number of pixels in one combination. Thus, deterioration of signal intensity obtained by the detector can be prevented. More specifically, since the frame rate and the number of pixels of the combination are determined based on the frequency characteristics (e.g., cutoff frequency) of the detector, deterioration of the signal intensity obtained by the detector can be surely prevented.

According to the present exemplary embodiment, the AOSLO image can be obtained while preventing light from a plurality of light sources from simultaneously entering into the subject's eye. Thus, reduction of image quality can be prevented while securing safety.

In the state in which the light emitted from the light source 201-3 enters into the subject's eye 207, the fixation lamp 256 is lit. Thus, movement of the subject's eye 207 can be suppressed, and aberration measurement can be accurately performed.

Further, entry of the measurement light emitted from the light source 201-2 into the subject's eye 207 is limited after storage of the WFSLO image and the obtaining position of the AOSLO image is adjusted using the WFSLO image, so that the light amount illuminating the subject can be reduced more.

According to the present exemplary embodiment, when the limitation of the entry of the measurement light into the subject's eye 207 is released, time from turning-off of the light sources 201-1 to 201-3 to stable emission of the light is made unnecessary. Thus, reduction of image quality can be prevented while securing safety, and inspection time can be prevented from being longer.

Since the open/closed states of the shutters 291-1 to 291-3 are displayed in the shutter state display region 509, the examiner can clearly and easily understand which of the measurement lights 206-1 to 206-3 is being applied to the subject's eye 207. Thus, certainty of the imaging operation can be improved.

The above-described exemplary embodiment is directed to eyes. However, the present invention can be applied to other portions such as skins or organs.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-126192 filed Jun. 1, 2012, which is hereby incorporated by reference herein in its entirety.

What is claimed is:
1. An ophthalmologic apparatus comprising:
   an aberration measurement unit configured to measure aberration caused by a subject's eye;
   a correction unit configured to correct aberration of return light from the subject's eye of measurement light applied to the subject's eye caused by the subject's eye based on the aberration measured by the aberration measurement unit;
   a storage unit configured to store a plurality of combinations of a frame rate for obtaining an image of the subject's eye with a number of pixels of the image; and
   an obtaining unit configured to obtain the image based on the frame rate and the number of pixels in one combination among the plurality of combinations using aberration-corrected return light from the subject's eye.

2. The ophthalmologic apparatus according to claim 1, further comprising a light receiving unit configured to receive return light from the subject's eye,
   wherein the frame rate and the number of pixels of the combination stored in the storage unit are values determined based on frequency characteristics of the light receiving unit.

3. The ophthalmologic apparatus according to claim 2, wherein a product of the frame rate and the number of pixels of the combination stored in the storage unit is smaller than the frequency characteristics of the light receiving unit.

4. The ophthalmologic apparatus according to claim 1, further comprising:
   a scanning unit configured to scan the subject eye with the measurement light; and
   a control unit configured to control the scanning unit so that the image is obtained by the frame rate in one combination among the plurality of combinations.

5. The ophthalmologic apparatus according to claim 1, further comprising a display control unit configured to cause a plurality of display units to display display forms indicating the combinations according to values of the frame rates.

6. The ophthalmologic apparatus according to claim 5, wherein the obtaining unit obtains the image by the frame rate and the number of pixels in the combination indicated by one display form selected from among the plurality of display forms displayed by the display units.

7. The ophthalmologic apparatus according to claim 6, wherein the display control unit sets at least one display form unselectable among the plurality of display forms displayed by the display units according to a type of measurement with respect to the subject's eye.

8. A method of controlling an ophthalmologic apparatus, the method comprising:
   measuring aberration caused by a subject's eye with an aberration measurement unit;
   correcting aberration of return light from the subject's eye of measurement light applied to the subject's eye caused by the subject's eye based on the measuring by the aberration measurement unit;
   storing a plurality of combinations of a frame rate for obtaining an image of the subject's eye with a number of pixels of the image; and
   obtaining the image based on the frame rate and the number of pixels in one combination among the plurality of combinations using aberration-corrected return light from the subject's eye.

9. The method according to claim 8, further comprising receiving return light from the subject's eye with a light receiving unit,
   wherein the frame rate and the number of pixels of the combination stored are values determined based on frequency characteristics of the light receiving unit.

10. The method according to claim 9, wherein a product of the frame rate and the number of pixels of the combination stored is smaller than the frequency characteristics of the light receiving unit.

11. The method according to claim 8, further comprising:
    scanning, with a scanning unit, the subject eye with the measurement light; and
    controlling the scanning unit so that the image is obtained by the frame rate in one combination among the plurality of combinations.

12. The method according to claim 8, further comprising controlling a plurality of display units to display display forms indicating the combinations according to values of the frame rates.

13. The method according to claim 12, wherein the obtaining includes obtaining the image by the frame rate and the number of pixels in the combination indicated by one display form selected from among the plurality of display forms displayed by the display units.

14. The method according to claim 13, wherein the controlling includes setting at least one display form unselectable among the plurality of display forms displayed by the display units according to a type of measurement with respect to the subject's eye.

15. A non-transitory computer-readable medium having stored thereon a computer program comprising program code having computer-executable instructions for causing a computer to execute the method according to claim 8.

16. An ophthalmologic apparatus comprising: an aberration measurement unit configured to measure aberration caused by a subject's eye;
    a correction unit configured to correct aberration of return light from the subject's eye of measurement light applied to the subject's eye caused by the subject's eye based on the aberration measured by the aberration measurement unit;
    a selection unit configured to select a frame rate for obtaining an image of the subject's eye; and
    an obtaining unit configured to obtain the image based on the selected frame rate and a number of pixels corresponding to the selected frame rate using aberration-corrected return light from the subject's eye.

17. The ophthalmologic apparatus according to claim 16, further comprising a light receiving unit configured to receive return light from the subject's eye,
    wherein the number of pixels is a value determined based on frequency characteristics of the light receiving unit.

18. The ophthalmologic apparatus according to claim 17, wherein a product of the frame rate and the number of pixels is smaller than the frequency characteristics of the light receiving unit.

19. An ophthalmologic apparatus comprising: an aberration measurement unit configured to measure aberration caused by a subject's eye;
    a correction unit configured to correct aberration of return light from the subject's eye of measurement light applied to the subject's eye caused by the subject's eye based on the aberration measured by the aberration measurement unit;
    a selection unit configured to select a number of pixels of an image of the subject's eye; and
    an obtaining unit configured to obtain the image based on the selected number of pixels and a frame rate corresponding to the selected number of pixels using aberration-corrected return light from the subject's eye.

20. The ophthalmologic apparatus according to claim 19, further comprising a light receiving unit configured to receive return light from the subject's eye,
    wherein the frame rate is value determined based on frequency characteristics of the light receiving unit.

* * * * *